(12) United States Patent
Barberio

(10) Patent No.: US 6,616,622 B1
(45) Date of Patent: Sep. 9, 2003

(54) SURGICAL CAST VENTING DEVICE

(76) Inventor: Alessandro Barberio, Suite 205, 4325 Steeles Avenue, West, North York, Ontario (CA), M3N 1V7

( * ) Notice: Subject to any disclaimer, the term of this patent is extended or adjusted under 35 U.S.C. 154(b) by 0 days.

(21) Appl. No.: 09/533,214

(22) Filed: Mar. 23, 2000

(51) Int. Cl.[7] .................................................. A61F 5/00
(52) U.S. Cl. ............................... 602/14; 602/5; 602/60; 602/78
(58) Field of Search .................................. 602/1–2, 3–8, 602/12, 14, 20–22, 44, 60, 78

(56) References Cited

U.S. PATENT DOCUMENTS

| | | | |
|---|---|---|---|
| 1,213,941 A | | 1/1917 | Patrick |
| 2,480,035 A | | 8/1949 | Lindstrom |
| 2,666,207 A | | 1/1954 | Lucas |
| 2,704,067 A | | 3/1955 | Moses |
| 2,731,963 A | | 1/1956 | Blank |
| 2,822,806 A | | 2/1958 | Blank |
| 3,116,731 A | | 1/1964 | Baxter |
| 3,307,537 A | | 3/1967 | Simon |
| 3,417,408 A | | 12/1968 | Caggiano |
| 3,656,477 A | | 4/1972 | Thomas |
| 3,701,349 A | | 10/1972 | Larson |
| 3,850,167 A | * | 11/1974 | Seeley ........................ 602/6 |
| 3,882,857 A | | 5/1975 | Woodall, Jr. |
| 3,930,496 A | | 1/1976 | Gibbons |
| 3,998,220 A | | 12/1976 | Cleer, Jr. |
| 4,308,862 A | | 1/1982 | Kalmar |
| 4,387,710 A | | 6/1983 | Beatty |
| 4,425,913 A | * | 1/1984 | Lewis ........................ 128/877 |
| 4,436,088 A | * | 3/1984 | Finnieston ................... 602/20 |
| 4,898,160 A | | 2/1990 | Brownlee |
| 5,086,518 A | | 2/1992 | Staley |
| 5,226,194 A | | 7/1993 | Staley |
| 5,468,219 A | * | 11/1995 | Crippen ........................ 602/6 |
| 5,511,323 A | | 4/1996 | Dahlgren |
| 5,527,265 A | * | 6/1996 | McKeel ........................ 602/6 |
| 5,916,184 A | * | 6/1999 | McKeel ........................ 602/6 |

* cited by examiner

Primary Examiner—Nicholas D. Lucchesi
Assistant Examiner—Lalita M. Hamilton
(74) Attorney, Agent, or Firm—Ridout & Maybee

(57) ABSTRACT

A surgical cast venting device comprises an elongate strip of porous fabric material and a number of relatively short, elongate plastic tubing members distributed over and attached to the elongate strip on one side thereof. The tubing members each extend substantially parallel to this one side and are open ended. The elongate strip can be wound around part of a human's body or an animal's body prior to application of a surgical cast. Preferably the tubing members each have ventilation holes distributed along their respective lengths. The fabric material can be gauze and the tubes can be attached thereto by adhesive. A multiple hook array fastener arrangement can extend along and be secured to a first longitudinal edge section and is adapted to detachably secure its edge section to a second, opposite longitudinal edge section when the fabric strip is wound around the body part. A number of different types of aerating devices that can be used instead of plastic tubing are also disclosed.

27 Claims, 32 Drawing Sheets

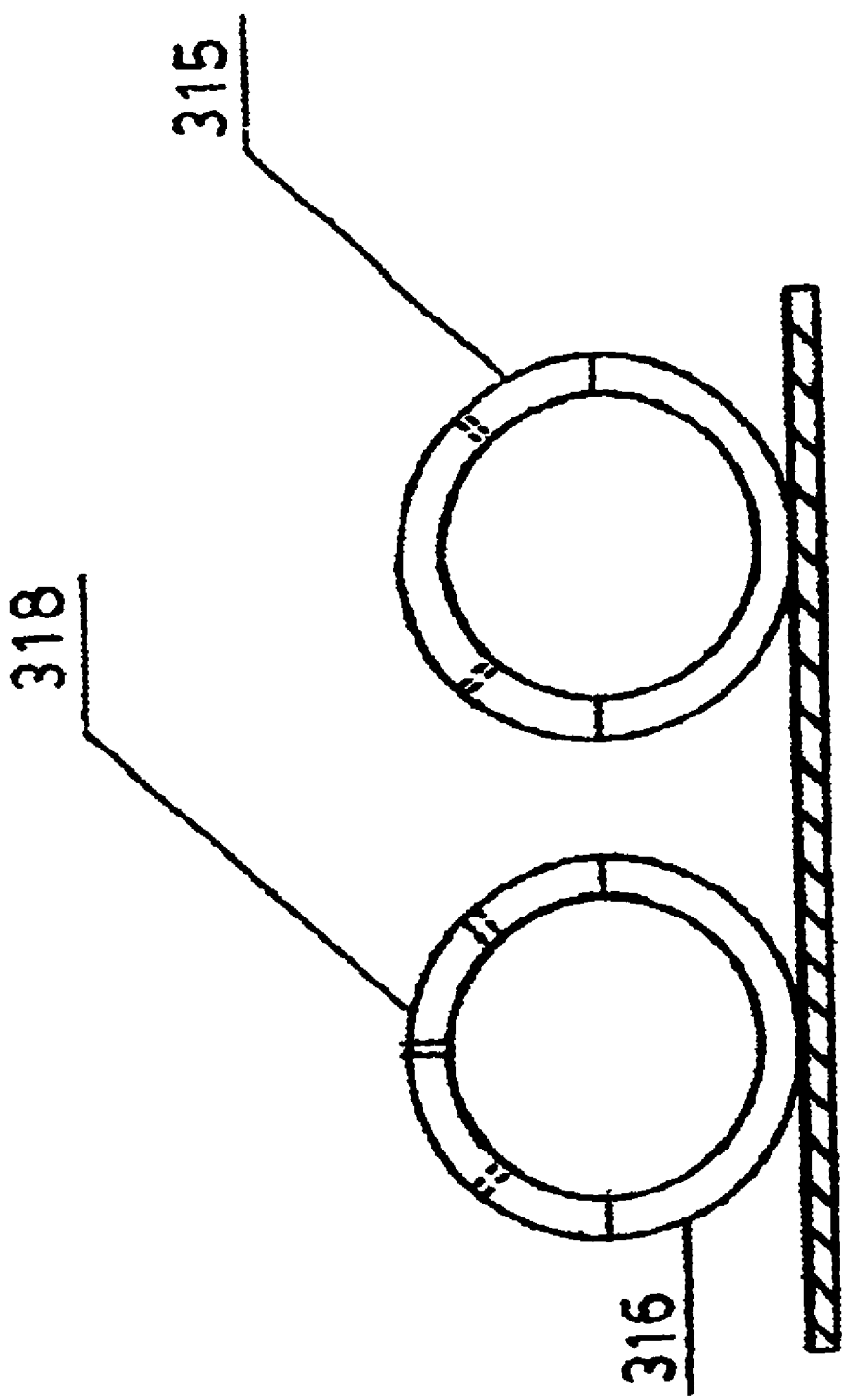

SURGICAL CAST VENTING DEVICE

BACKGROUND OF THE INVENTION

This invention relates to devices for venting a surgical cast.

In the attempt to solve the problem of supplying ventilation to skin under a surgical cast, a variety of different structures and methods have been disclosed. The common construction of surgical cast venting devices includes woven fabric along with an elongate tube or other such air passageway, in contact with skin, over which the plaster of paris mix casting material can be placed to form the cast. Also, a device forcing air under the cast can be provided. For example, an air pump could be provided.

U.S. Pat. No. 4,308,862 issued Jan. 5, 1982 to Irene Kalmar describes a plaster cast with a venting device. Plastic tubing is wrapped in a helix over the dressed area upon which a hardening material is placed. In addition, the conduits have regularly spaced holes along their inner surface which is flat. A hose connector protrudes from the conduit in the middle of the cast. A hose and air pump can be used to force air through the conduit. Also, a small amount of disinfectant can be pumped into the conduits.

U.S. Pat. No. 4,387,710 issued Jun. 14, 1983 to John C. Beatty, III teaches a ventilated cast structure and method for producing the same. An air conduit provides air to a domed cap, this cap providing the interface to the surgical cast venting device. In particular, this device includes a snap socket assembly with a plurality of air passages to provide air to a porous air distribution layer below the cast itself.

SUMMARY OF THE INVENTION

The present invention provides a surgical cast venting device which can be constructed in the form of a strip. The strip is elongate and made of porous fabric, gauze or casting material. Aeration devices such as plastic or latex tubing are attached at regular intervals along the woven fabric or casting material.

According to another aspect of the invention, a surgical cast venting device comprises an elongate porous woven fabric strip, a number of flexible, elongate tubes with holes distributed along their respective lengths, these tubes being distributed along the length of and attached to the fabric strip on one side thereof, each tube extending lengthwise in a direction substantially parallel to this one side. The elongate strip is suitable for winding around part of a human body or an animal's body prior to application of a surgical cast over this part of the body.

According to a further aspect of the invention, a surgical cast venting device comprises an elongate, flexible strip of thin porous material and a number of relatively short, elongate tubing members distributed over and mounted on the elongate strip on one side thereof. The length of each tubing member extends substantially parallel to this one side. The elongate strip with the tubing members is adapted for winding around part of a human body or an animal's body prior to application of a surgical cast over this part of the body.

In a preferred embodiment of the venting device, there are holes along the length of the tubes. Also, the tubes are round or oval shaped in cross-section.

In order to use the device, the elongate strip is wound around a human's or animal's arm or leg, such that the side of the strip to which the tubes are applied completely covers an area of dressed skin. Once the strip has been wound, it can be secured in place by Velcro strips, for example. The plaster is applied over the venting device. The cast then hardens and the cast is then completed. The natural movement of a person's or animal's muscles under the cast will serve to vent the cast if the venting device of the invention is properly arranged under the cast.

According to still another aspect of the invention, a surgical cast venting device comprises an elongate porous fabric strip having two opposite ends, having two opposite, longitudinal side edge sections, and having inner and outer surfaces. Aerating devices are affixed to and located on the inner surface. A multiple hook array fastener arrangement extends along and is secured to a first of the longitudinal side edge sections and is adapted to detachably secure this first longitudinal side edge section to a second of the longitudinal side edge sections when said fabric strip is wound around part of the human or animal body prior to application of a surgical cast over this part of the body.

Preferably the elongate strip is tapered at the ends. With respect to the tubes on the strip, they can be attached at a slight angle to a line extending transversely across the strip. One third of the width of the strip is covered by the tubes, except near the ends of said strip.

A hose can be applied at one end of the cast. By applying a hose to one end of the cast and blowing air through the hose, air will flow in one end of the cast and escape through the other end providing ventilation to the cast. The air source attached to the hose can be an air pump.

A hair dryer can provide an air source analogous to that mentioned above. In order to achieve results equivalent to the hose method, the dryer can be provided with a special attachment allowing air to be forced under the cast.

Further features and advantages will become apparent from the following detailed description of a preferred embodiment taken in conjunction with the accompanying drawings.

BRIEF DESCRIPTION OF THE DRAWINGS

FIG. 35 is an end view illustrating a section of a venting device made with the tubes of FIG. 34.

DETAILED DESCRIPTION OF PREFERRED EMBODIMENTS

Figure 1:
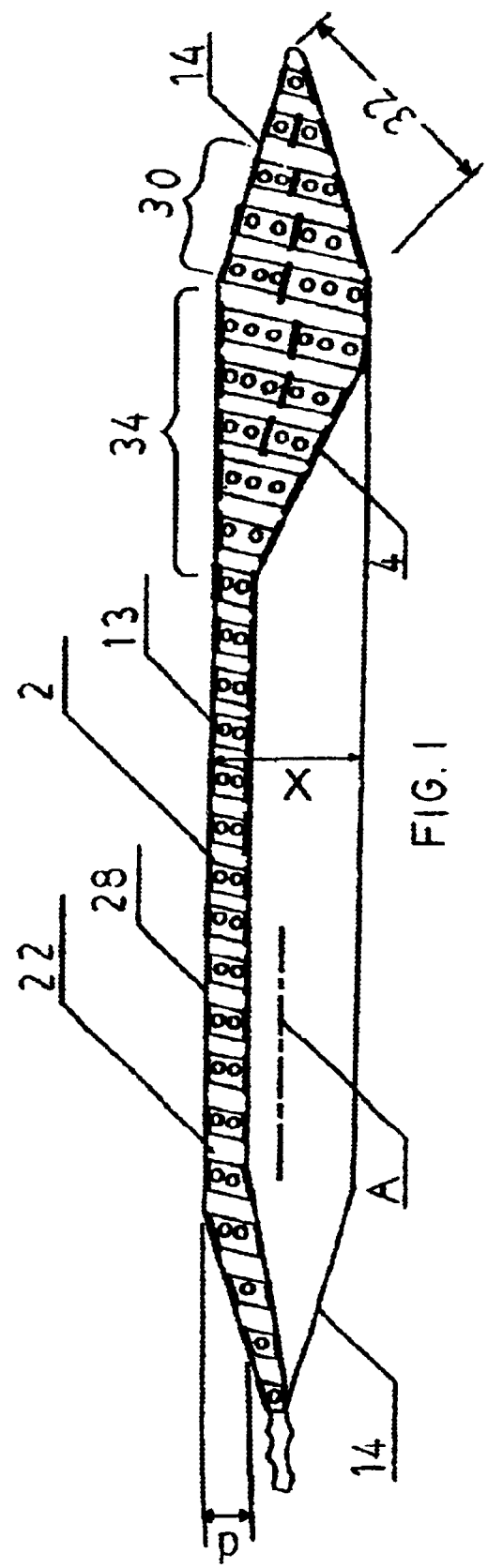
FIG. 1 is a plan view showing a surgical cast venting strip.
Figure 12:
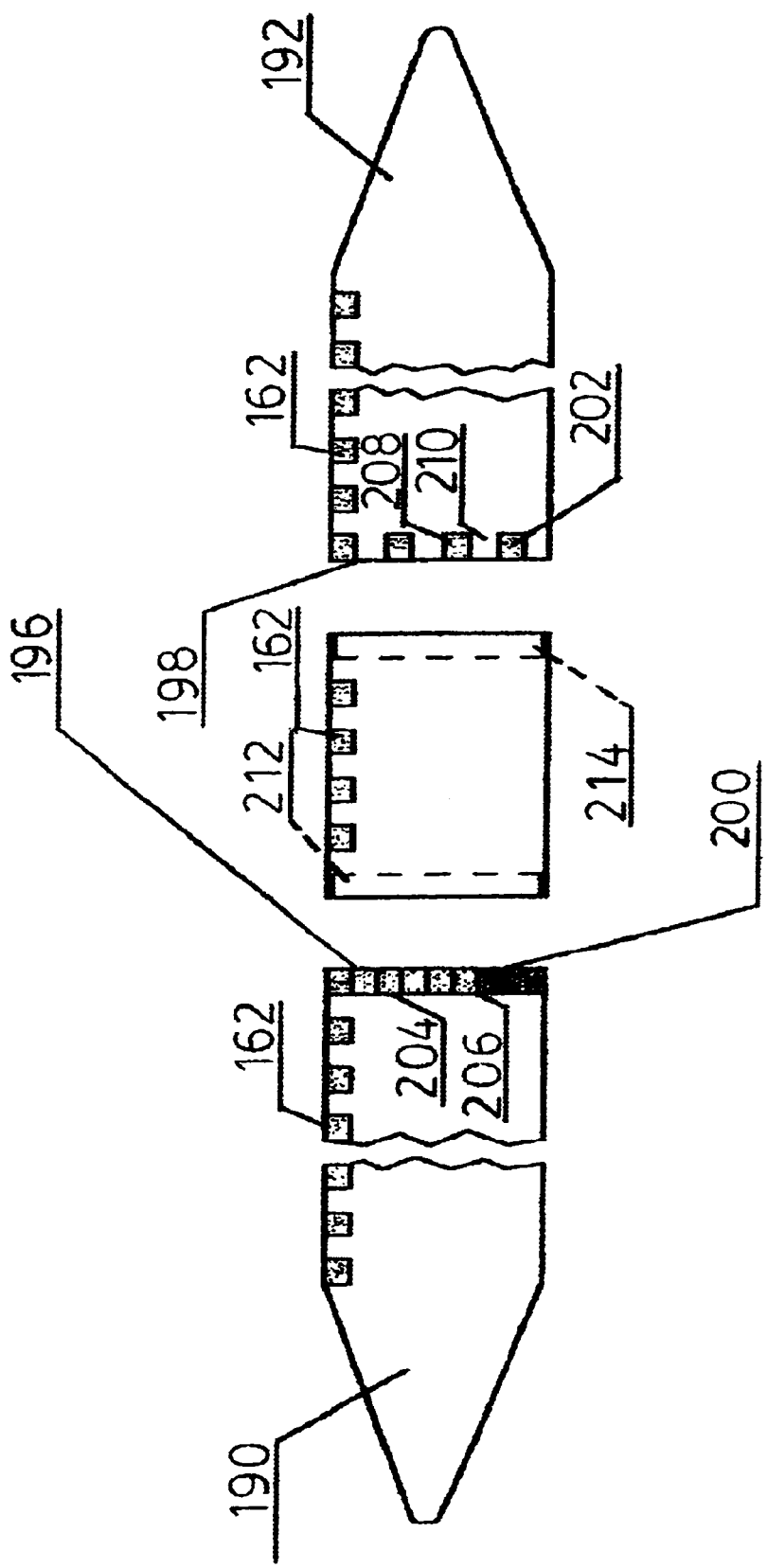
FIG. 12 is a plan view of the outer surface of three separate components that can be connected together to form a long surgical cast venting strip with central portions of the two end components being omitted to indicate indefinite length.

Shown in FIG. 1 is a preferred form of surgical cast venting device 1 that includes an elongate strip 22 of porous fabric material, preferably a woven fabric. One suitable form of material is a gauze material similar to that used to make bandages. The length of strip 22 can vary and will depend to some extent on the particular cast that it is to be used with. In a situation where strip 22 proves to be of insufficient length, one or more of the strips can be attached end to end, for example, by means of Velcro fastening strips as illustrated in FIG. 12. A number of relatively short, elongate plastic tubing members 2 are distributed over and attached to the elongate strip on one side 24 thereof. The tubes are preferably 7 to 10 mm in external diameter and can be open ended. Preferably the plastic from which the tubes are made is reasonably flexible so that the cast venting device will be comfortable when applied in the manner described hereinafter. The elongate strip with the attached tubing members is adapted for winding around part of a human body (such as an arm or leg) or an animal's body that has been injured prior to application of a surgical cast over this part of the body.

Figure 3:
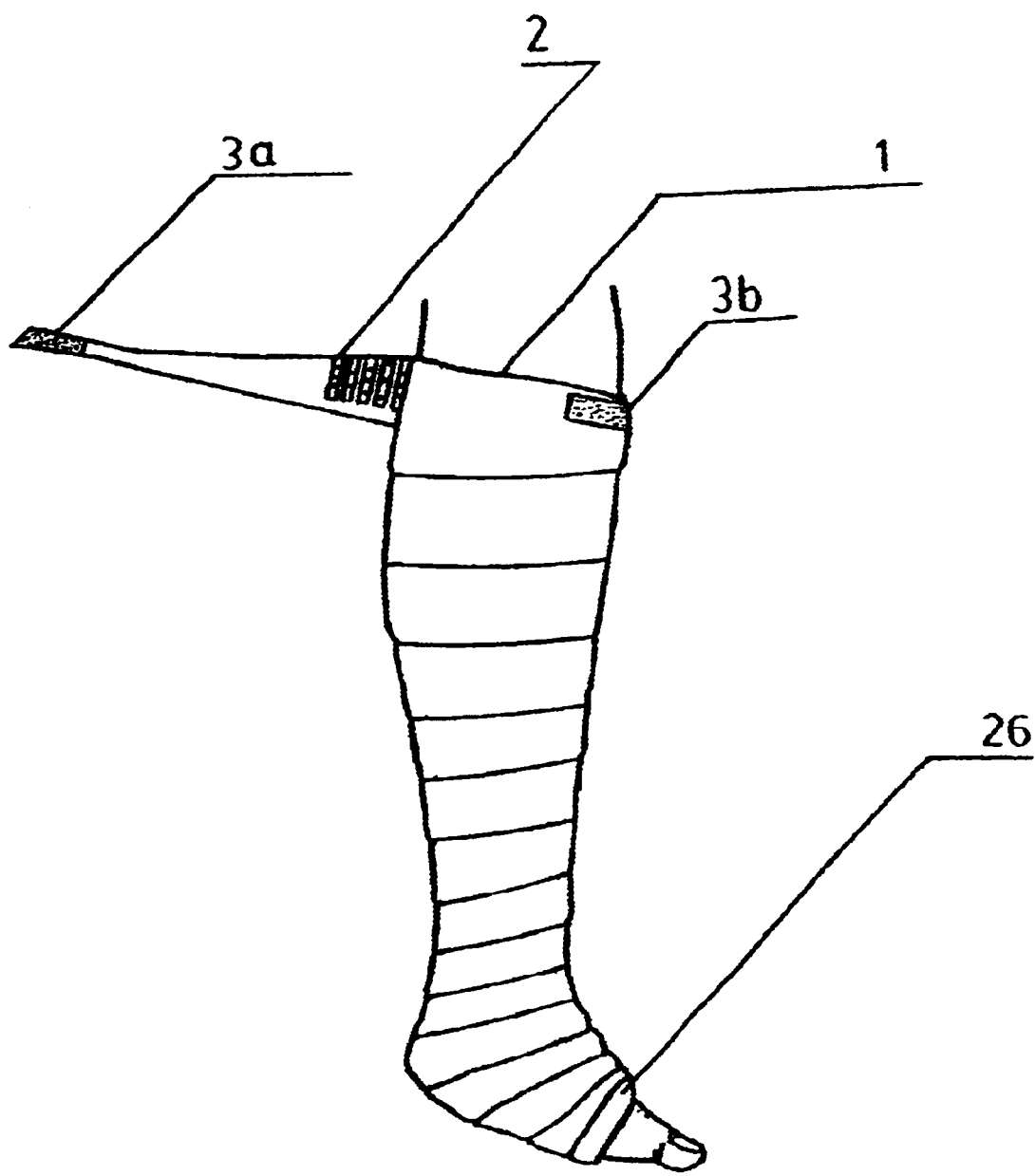
FIG. 3 is a side view of the cast venting device applied and wrapped around a human leg.

Preferably plastic tubing members 2 each have a number of small holes 13 distributed along their respective lengths so as to permit the passage of air in and out of the tubing members. These holes 13 can, for example, be arranged in several rows along the length of the tubing members, if desired, in order to provide good ventilation. FIG. 3 illustrates how the venting device 1 of the invention can be wrapped around the leg of a human, for example, one that has been broken. The venting device as shown is wrapped first around the foot at 26 and is then wrapped in a partially overlapping manner as shown until the venting device is completely wrapped around the body part. Also note that the side with the plastic tubing members attached thereto is the side facing towards the leg. If desired, and for increased comfort, a suitable cloth or fabric sleeve can be placed snugly over the foot and leg prior to the wrapping of the cast venting device thereon. Such body sleeves for placement next to the skin are already well known in the cast making art.

The wraps formed by the venting device should be arranged so that the tubing members 2 are not wrapped on top of one another. In other words, the tubing members when the cast venting device has been put in place, should be distributed reasonably evenly and in a single layer only over the area to be covered with the cast. Also, in a preferred version of the strip, the distance between adjacent tubes is about equal to the diameter of the tubes themselves but this distance will increase slightly as the strip is stretched.

For the proper application of the venting device in the described continuous wrapped manner, the preferred venting device is constructed in the manner illustrated in FIG 1. Firstly, it will be noted that the elongate strip 22 is tapered at 14 at opposite ends thereof. As shown, each end tapers inwardly in a direction away from the longitudinal center of the strip. Also, for a substantial portion of the length of the elongate strip, the plastic tubing members 2 extend from one long edge 28 of the strip a distance which does not exceed one half the width of the strip, this distance being indicated by the dimension d in FIG. 1. In fact, in the illustrated embodiment, the distance d is about one third the maximum width of the fabric strip from the long edge 28. This maximum width is denoted x, and can vary depending of the region of the body to which the device is applied. When the strip is to be wound around a straight portion of a leg, x is preferably about 4 inches. When the strip is to be wrapped around a bend such as a knee, x can be somewhat greater, about 4.5 inches.

At one end of the strip the plastic tubes can extend further as shown in FIG. 1, this being the end where the wrapping operation commences. Thus, the tubing at 30 extends substantially the entire width of the strip 22. Also, the tubing at 32 located at the tapered end 14 can extend the entire width of this tapered portion. In the region 34 of the strip that extends between the region 30 and the much longer region where the tubes are of substantially the same short length, the tubes can gradually shorten in length to provide a transition region. At the opposite end, the tubing members can be quite short and extend only part way across the strip. With the tubing members arranged in the optimal manner, each wrap of the venting device (see FIG. 3) can be made to overlap the previous wrap a substantial distance without resulting in the tubing members being laid on top of each other. In other words, if the tubing members extend only one third of the width of the strip for most of the length of the strip, then the uncovered portion 40 of the strip, will overlap the adjacent and underlying wrap of the strip. In this way, the wrapped venting device 1 will form a securely wrapped sleeve about the leg or arm and each wrap of the venting device will be held firmly in place prior to the application of the casting material.

As shown in FIG. 1, the plastic tubing members 2 can be attached or bonded to the strip 22 at a small acute angle to a transverse line (for example, the An illustrated line X) perpendicular to a longitudinal central axis A of the elongate strip. In the alterative, the tubes can be arranged so that their length extend perpendicular to the longitudinal central axis A, this arrangement being shown in FIG. 2.

Figure 9:
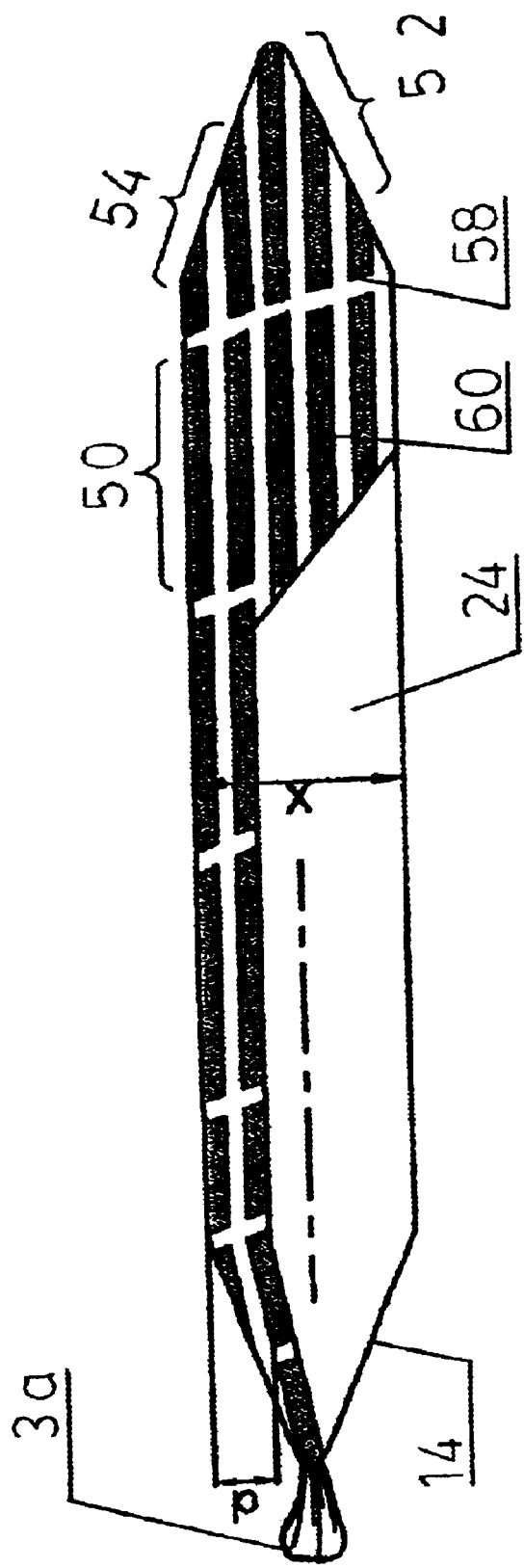
FIG. 9 is a plan view similar to FIG. 1 but showing an alternate embodiment of the cast venting strip of the invention.

It is also possible to construct the present cast venting device as shown in FIG. 9 using longer plastic tubing members 60 that extend substantially in the longitudinal direction of the fabric strip. These tubing members can be aligned end-to-end in rows as shown and would have sufficient flexibility to readily bend along body contours. Again, the tubing in the region 54 is distributed evenly across the entire width of the fabric strip. Also, the tubing at 52 located in the region of the tapered end is evenly spaced across the entire width of this tapered portion with the tubes parallel to the longitudinal axis. In the region 50 of this device, the tube lengths are gradually shortened to provide a transition region. These longer plastic tubes can also be open ended at their ends 58.

It will be particularly noted from FIG. 9 that the long tube members are interrupted by short spaces between adjacent ends 58. These space interruptions are aligned at an acute angle to the longitudinal centerline of the strip 22. This acute angle is selected and used to give more freedom when the venting device is wrapped around a body part or limb and makes the device easier to wrap.

Preferably the cast venting device is equipped with means for securing the fabric strip in place after the fabric strip has been wound around the body part. Although a variety of securing devices are possible, one preferred form of securing device includes hook and loop type fastening strips attached at one or both ends of the fabric strip. These well known types of fasteners are sold under the VELCRO trade-mark and they are indicated at 3a and 3b in FIGS. 2 and 3. The strip 3a is one half of the fastener system and consists of a strip with a gridwork of small hooks formed thereon as is well known in the fastening art. The strip 3b, which is attached to the opposite side of the strip 22 and can be located a distance from the end of the strip can be a strip covered with small loops which are easily engaged by the hooks on the strip 3a. Provided the strip 22 is made from a suitable porous fabric material that can be readily engaged by the hooks on the strip 3a, one could, in the alternative, omit the strip 3b and simply attach the strip 3a to the outer side of the strip 22. Other types of securing means (not shown in the drawings) could include metal or plastic snap fasteners or simply cloth or rope tying members. It will be appreciated that the length of the elongate strip 22 can be made adjustable, if desired. One way of making it adjustable is described in detail below.

The plastic tubing members 2 can be attached in a permanent manner to the strip 22 by means of a suitable adhesive. The adhesive should be selected so as to be compatible with both the material of the strip 22 and the plastic from which the tubing is made and should provide a secure bond to both types of material.

Figure 2:
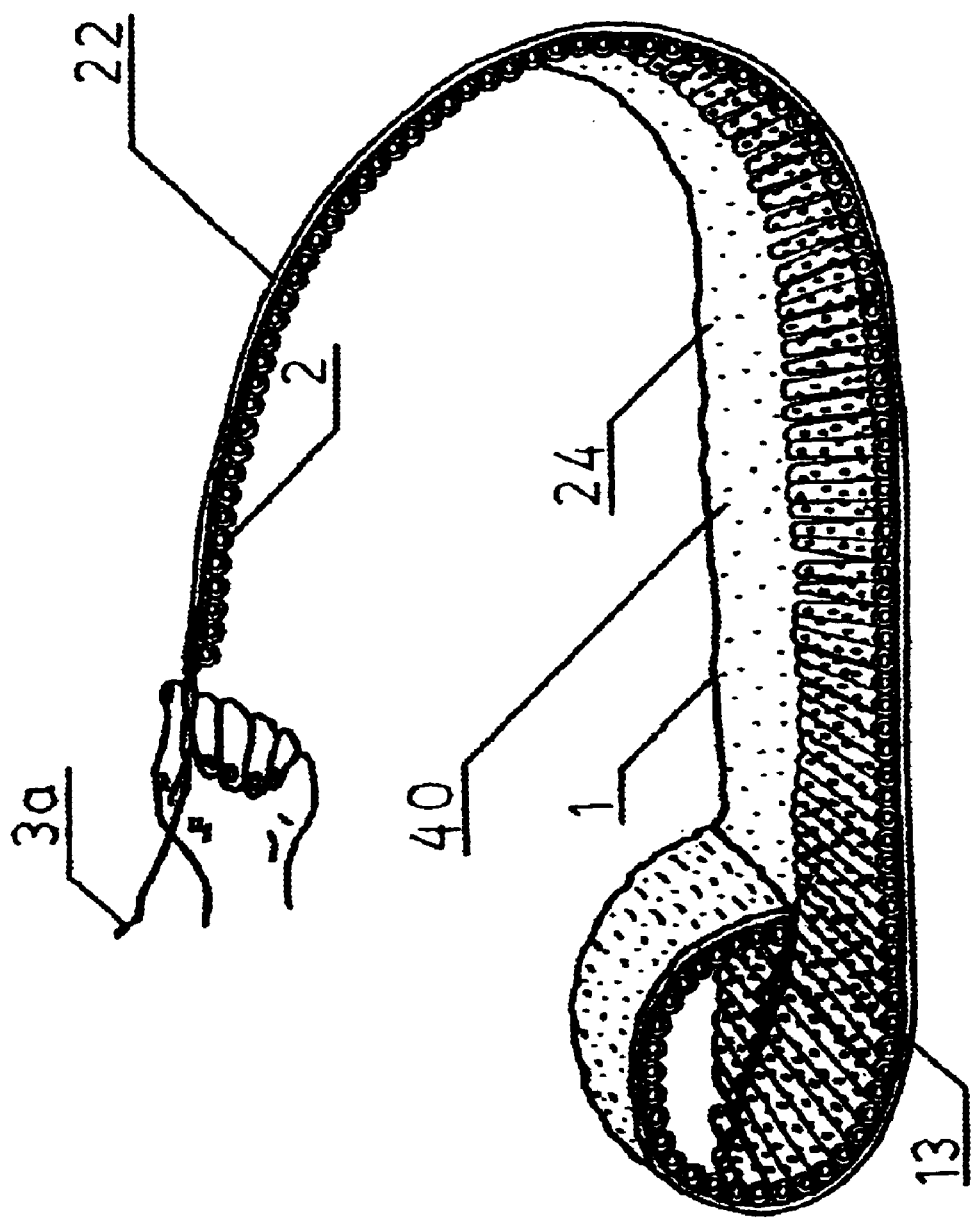
FIG. 2 is a perspective view of the surgical cast venting strip being unrolled.

As illustrated clearly in FIG. 2, in the preferred embodiment of the venting device the elongate tubes 2 are arranged so that their longitudinal central axes are substantially parallel when the fabric strip is laid out flat and straight and the tubes are arranged only a short distance apart from the adjacent tubes, for example, a distance of about the diameter of each tube.

Figure 4:
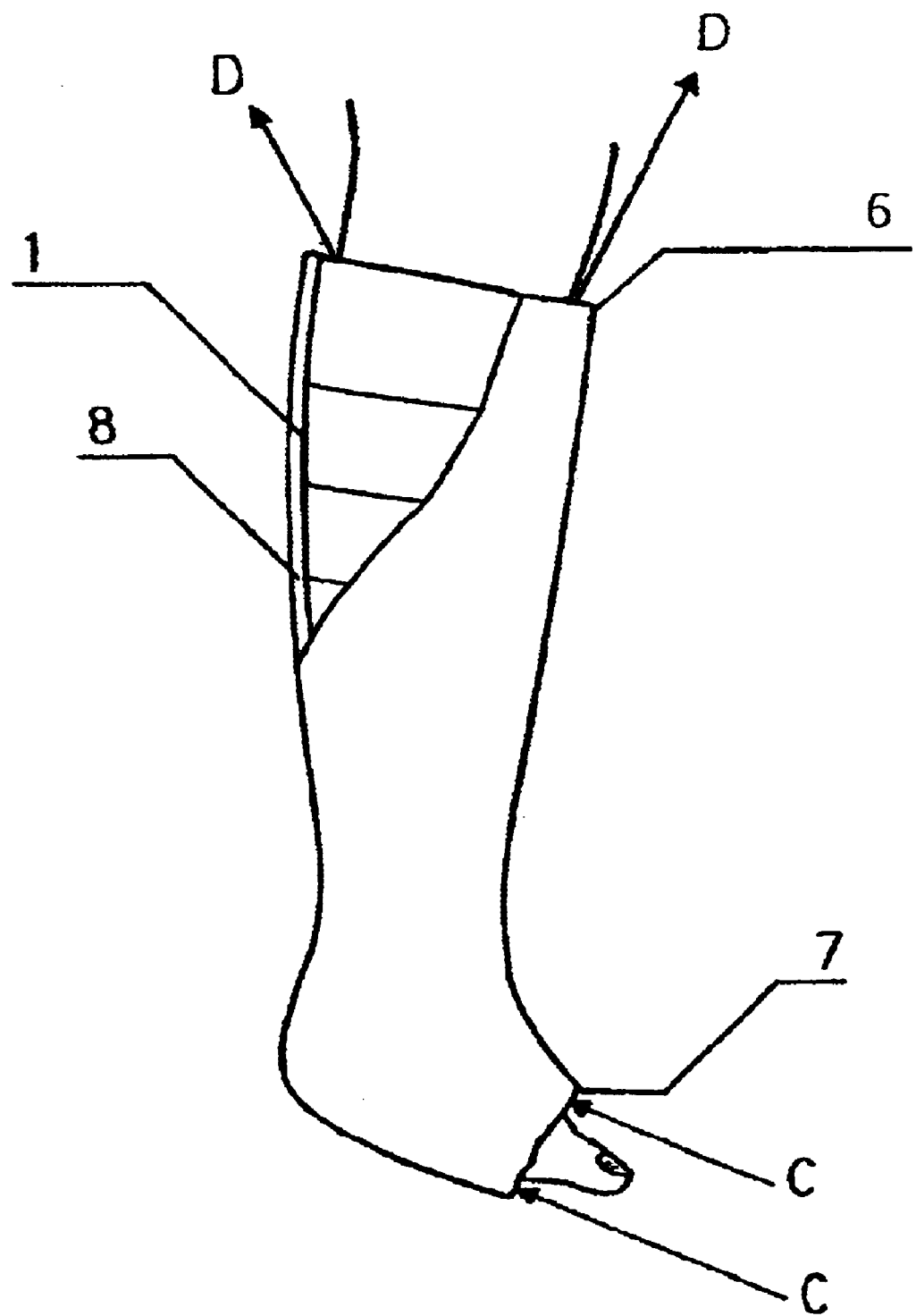
FIG. 4 is a cut away elevational view of the surgical cast venting device covered by a hardened cast, the latter being partially cut away for sake of illustration.

In order to use the present venting device 1, the injured body part (after the bone has been reset) is suitably covered with a thin cloth or jersey material in a known manner. Then the venting device 1 has been wrapped around the injured body part and put in place. Note that the plastic tubes are located on the inner surface of the wrapped venting device, adjacent to the cloth or jersey material. Next the usual casting material 8 is placed over the venting device as illustrated in FIG. 4. Once this casting material has set, a rigid cast is formed about the venting device, thus protecting the injured limb and allowing it to heal. The casting material 8 can, for example, be made of a known plaster composition. Note that the casting material 8 has been omitted from FIGS. 5 and 6 in order to show the underlying venting device 1.

With the use of the present venting device, natural venting or aeration of the skin under the cast will occur simply as a result of normal muscle movement. Because the preferred venting device is made from flexible, pliable material, some limited degree of movement of the muscles in the leg or arm is permitted by this device and this will result in some movement of air into and out of the venting device as indicated by the arrows at C and D in FIG. 4. For example, the muscle movement may cause air to enter at the bottom 7 of the cast as indicated by the arrows C and cause a corresponding amount of air to exit from the top 6 of the cast as indicated by the arrows D.

Figure 5:
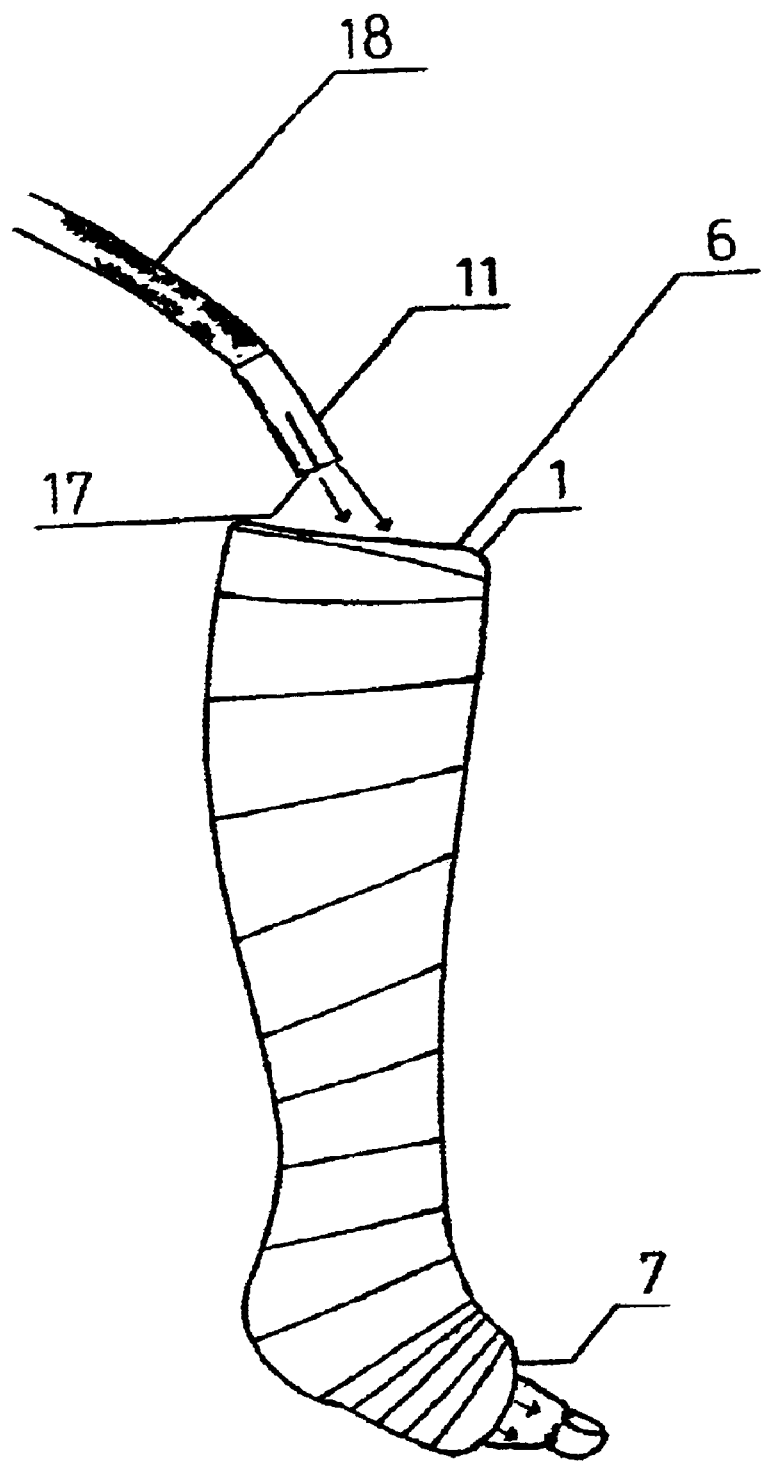
FIG. 5 is a side view of the surgical cast venting device and showing an air hose being applied to vent the device.
Figure 6:
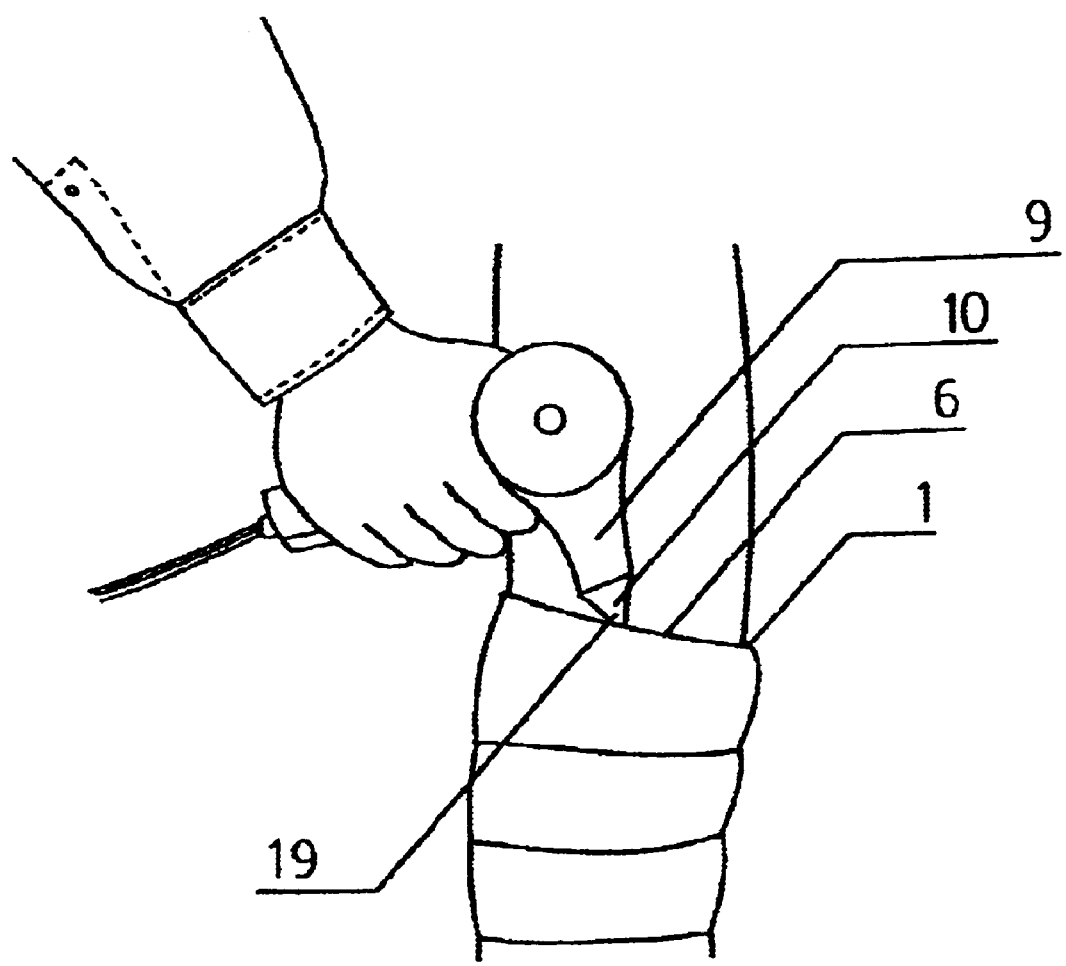
FIG. 6 is a side view of an upper portion of the surgical cast venting device showing a hair dryer being used to vent the device.

Further increased venting of the cast can be caused by using the methods illustrated in FIGS. 5 and 6 of the drawings. In FIG. 5, air is being forced into the top end 6 of the venting device by means of an air hose 18 having a nozzle 11 with a narrow end 17. Pressurized air could for example be provided to the hose 18 by means of a suitable compressor attached thereto. Air directed into the top of the venting device at 6 will eventually pass through the entire length of the venting device and exit at the bottom end 7.

FIG. 6 illustrates how a standard hair dryer 9 can be used to force air through the venting device of the invention. The hair dryer can be provided with a special outlet attachment 10 with a narrow, flat outer end at 19. As illustrated, air can be again forced into the top end of the venting device by placing the end 19 adjacent this upper end of the venting device and operating the hair dryer. The fast air flow will eventually pass through the length of the venting device and exit through the bottom end thereof.

Figure 7:
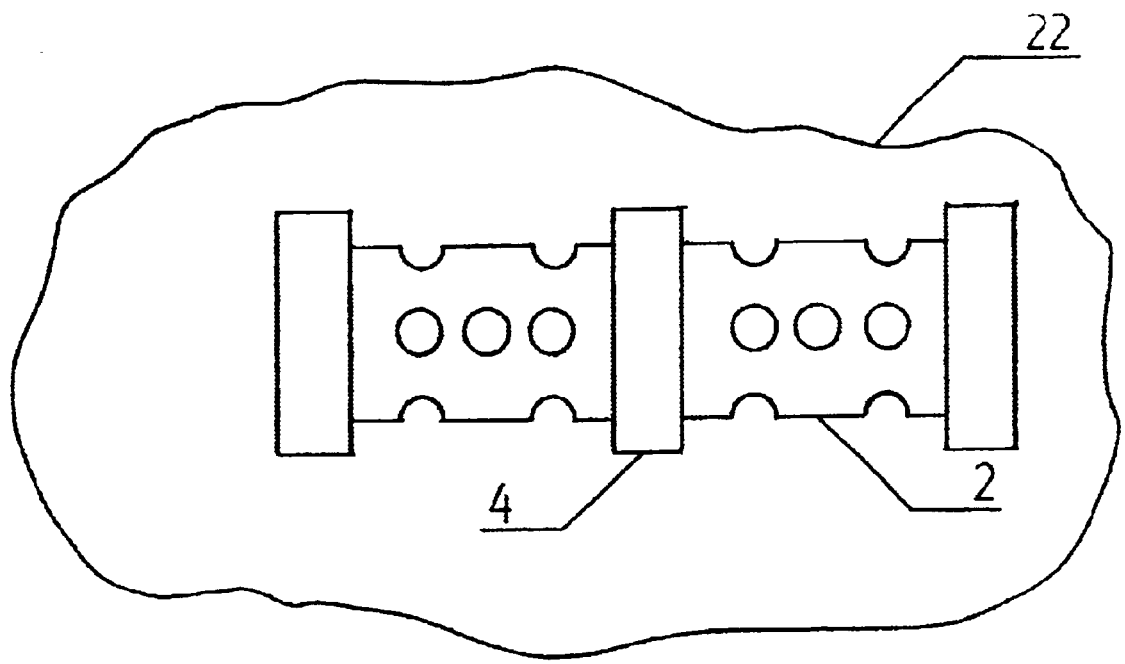
FIG. 7 is a side view of an alternative construction for the plastic tubing members.
Figure 8:
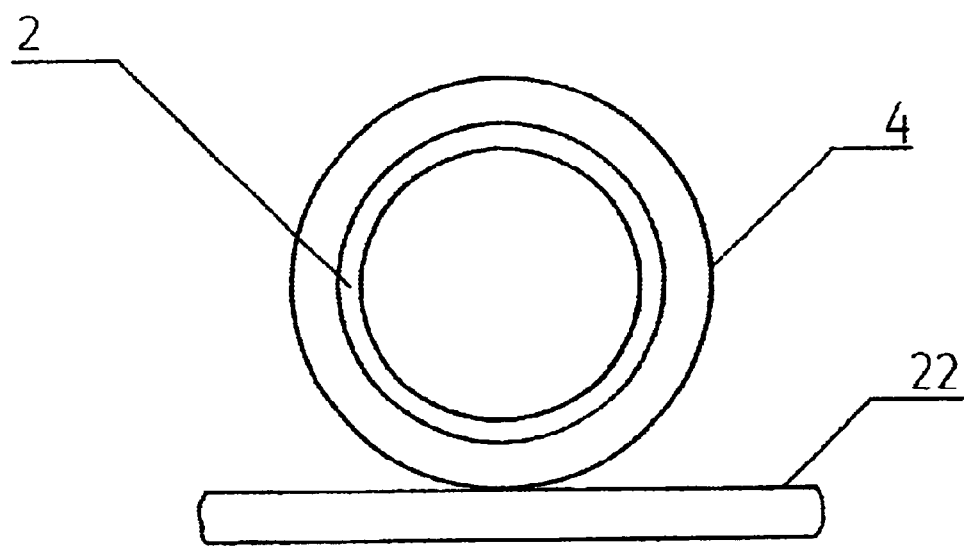
FIG. 8 is an end view of the alternative tubing member of FIG. 7.

FIGS. 7 and 8 illustrate in detail a preferred feature for the tubing of the venting device. The plastic tubing members 2 are partially surrounded with sponge strips 4. As illustrated, there can be two strips 4 located at opposite ends of each tubing member 2 and a central strip 4 positioned midway between the end strips. The purpose of these sponge strips is to provide more comfort to the user as they create a small gap between the plastic tubing and the user's skin or the cloth cover or sleeve. These strips also provide more aeration between the body of the user and the cast. The strips can be adhesively attached to the tubing.

Figure 31:
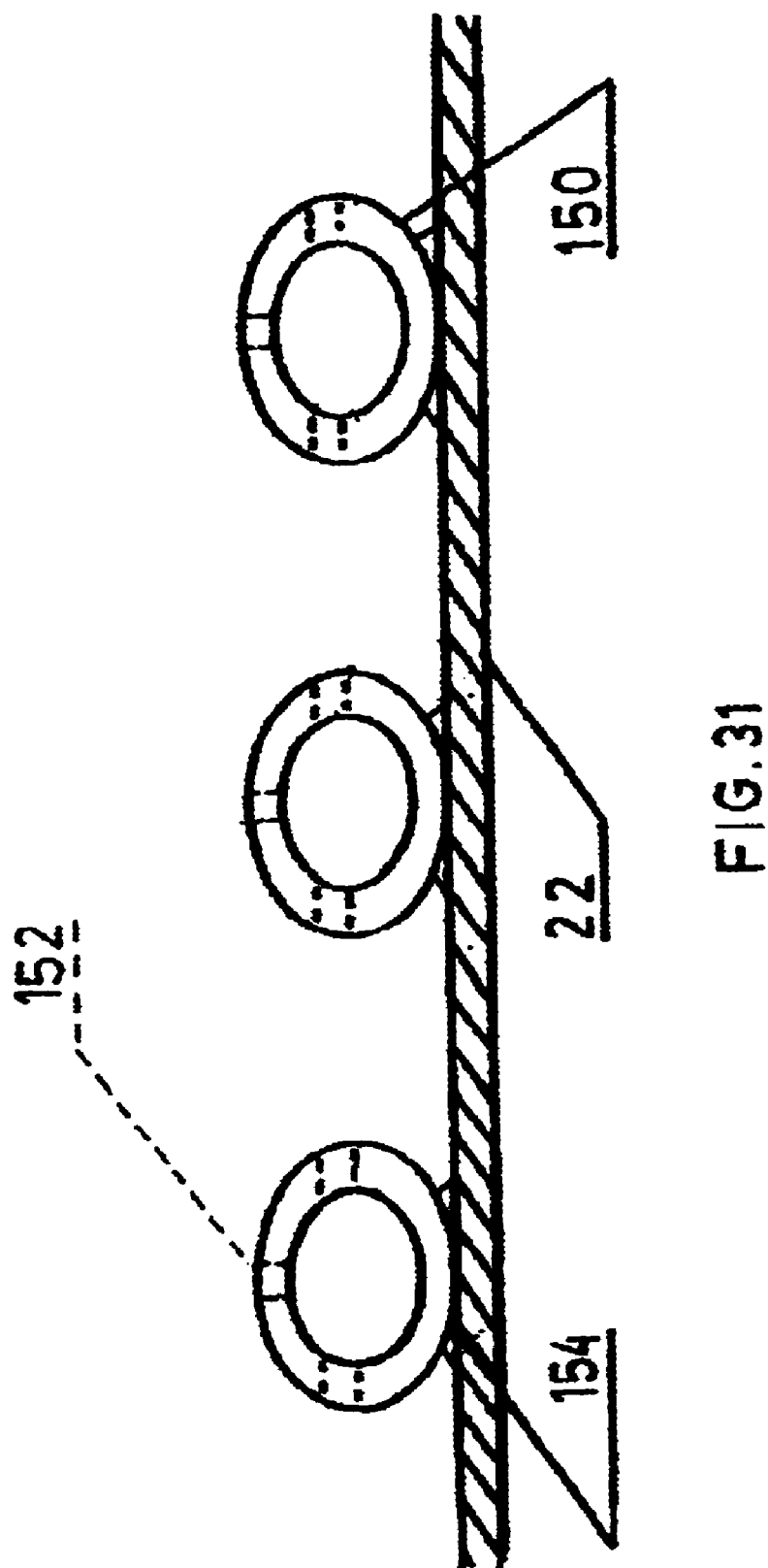
FIG. 31 is an edge view illustrating plastic tubular members having an oval cross-section, such members being usable in still another version of the invention.

The tubing members 2 may not necessarily be made of a flexible plastic material but they could also be made of other materials such as a flexible latex material. The tubes can have a cross-section other than round and they could, for example, have an oval cross-section as shown in FIG. 31.

Figure 10A:
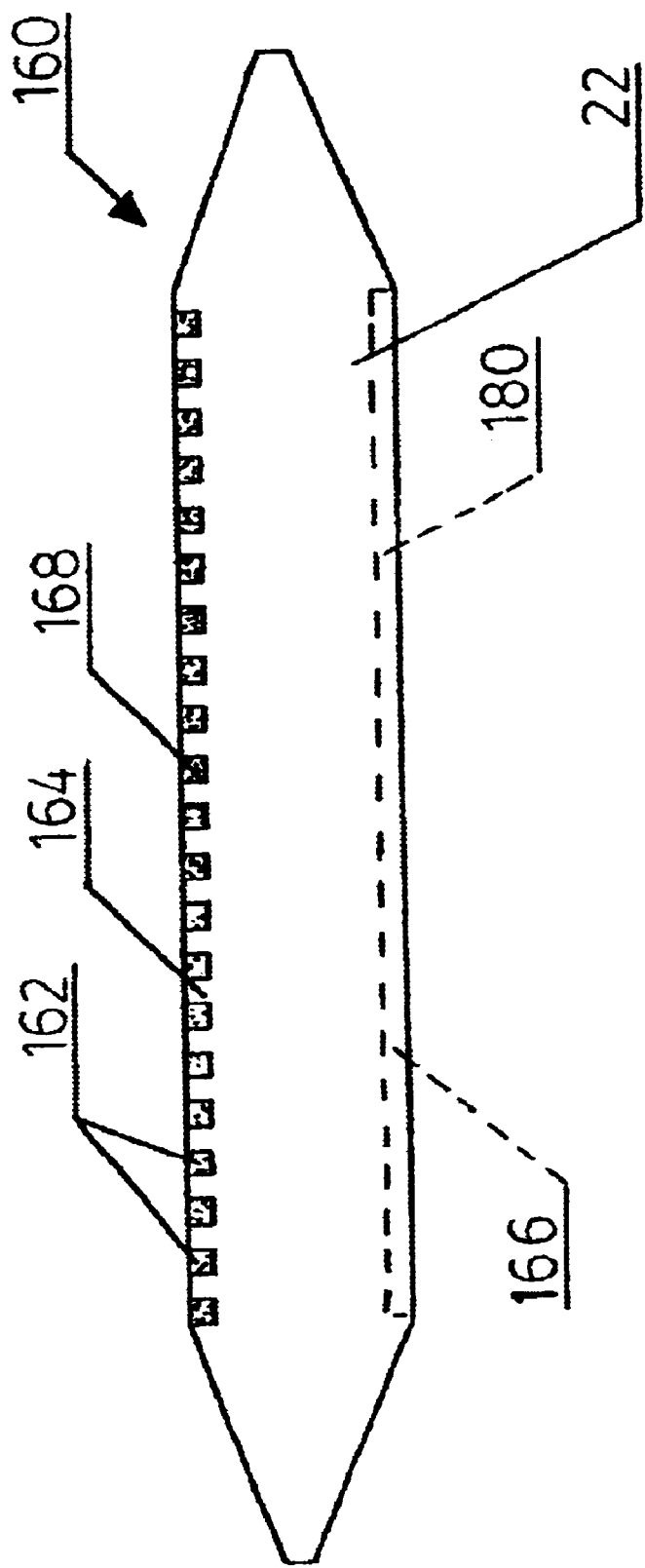
FIG. 10A is a plan view of the outer surface of another version of the surgical cast venting strip of the invention.
Figure 10B:
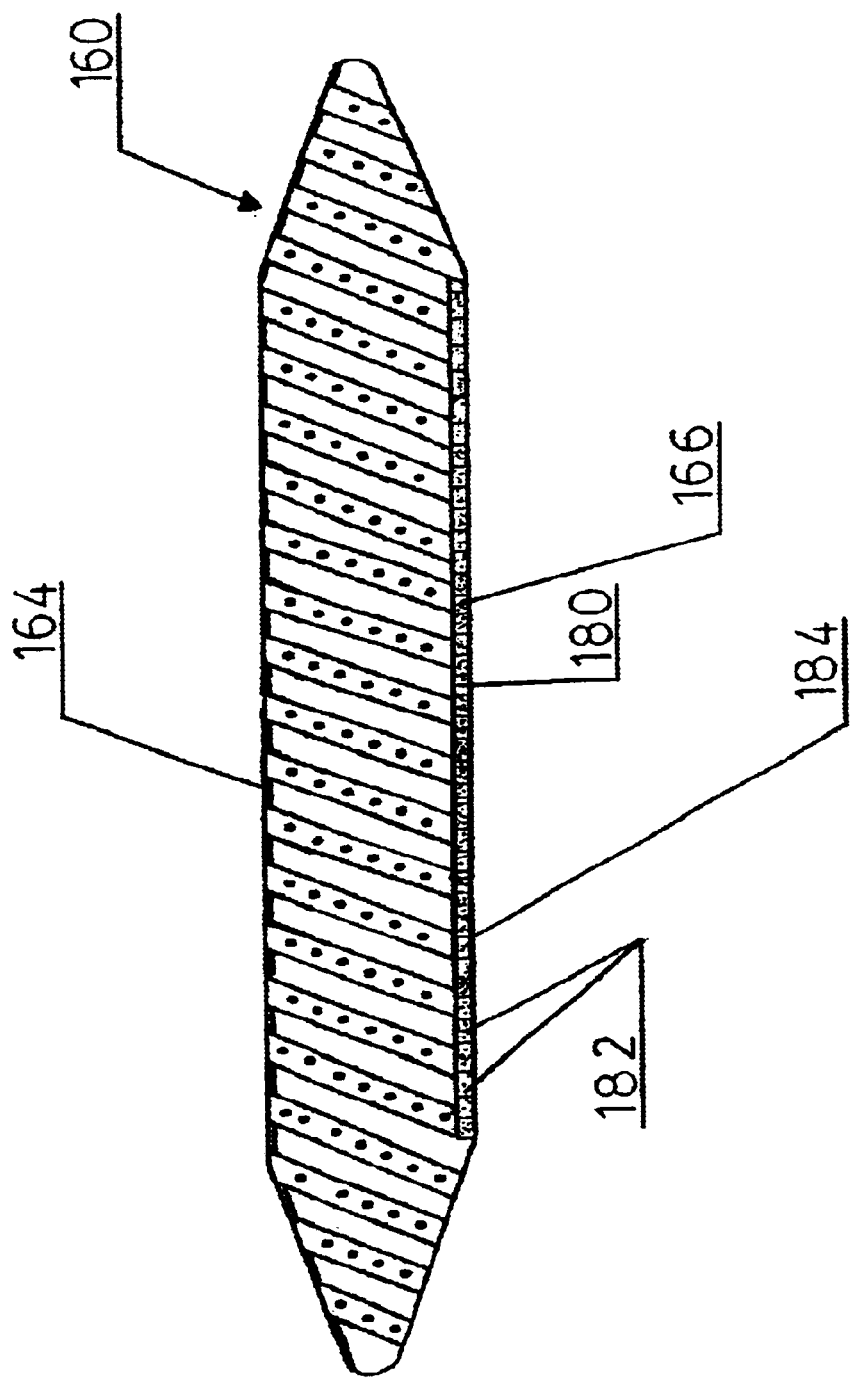
FIG. 10B is a plan view of the inner surface of the venting strip of FIG. 10A.

Another preferred form of surgical cast venting device constructed in accordance with the invention is illustrated in FIG. 10A and 10B of the drawings. This venting device 160 is similar to the venting device 1, illustrated in FIGS. 1 and 2, except for the differences noted hereinafter. In particular, this venting device includes a multiple hook array fastener arrangement indicated generally at 162 that extends along and is attached to a first longitudinal edge section 164 of the elongate strip of porous fabric material 22. The arrangement 162 is adapted to detachably secure the longitudinal edge section 164 to an adjacent second longitudinal edge section indicated at 166 when the elongate strip of material is wound around the part of the human body that is to be enclosed by a cast. In fact, the second longitudinal edge section is the edge section extending along the opposite longitudinal edge of the strip. In the embodiment illustrated in FIG. 10A, the hook array fastener arrangement comprises a series of spaced apart, hook array fastener devices or pads 168 distributed along the first longitudinal edge section. Preferably these fastener devices are attached to the edge section by bonding using suitable adhesive or by being stitched thereto using a suitable, stretchable elastic thread. It will be understood that the preferred elongate strip 22 is made with a fabric material which can be stretched to some extent as it is wound around the body part, thus allowing it to fit snugly. Although the hook array fastener devices or pads 168 may not themselves be stretchable, by spacing these devices apart, for example by the length of the pads themselves and by attaching the fastener devices using elastic thread, the ability of the elongate strip 22 to stretch during use is not substantially or detrimentally affected.

Figure 11:
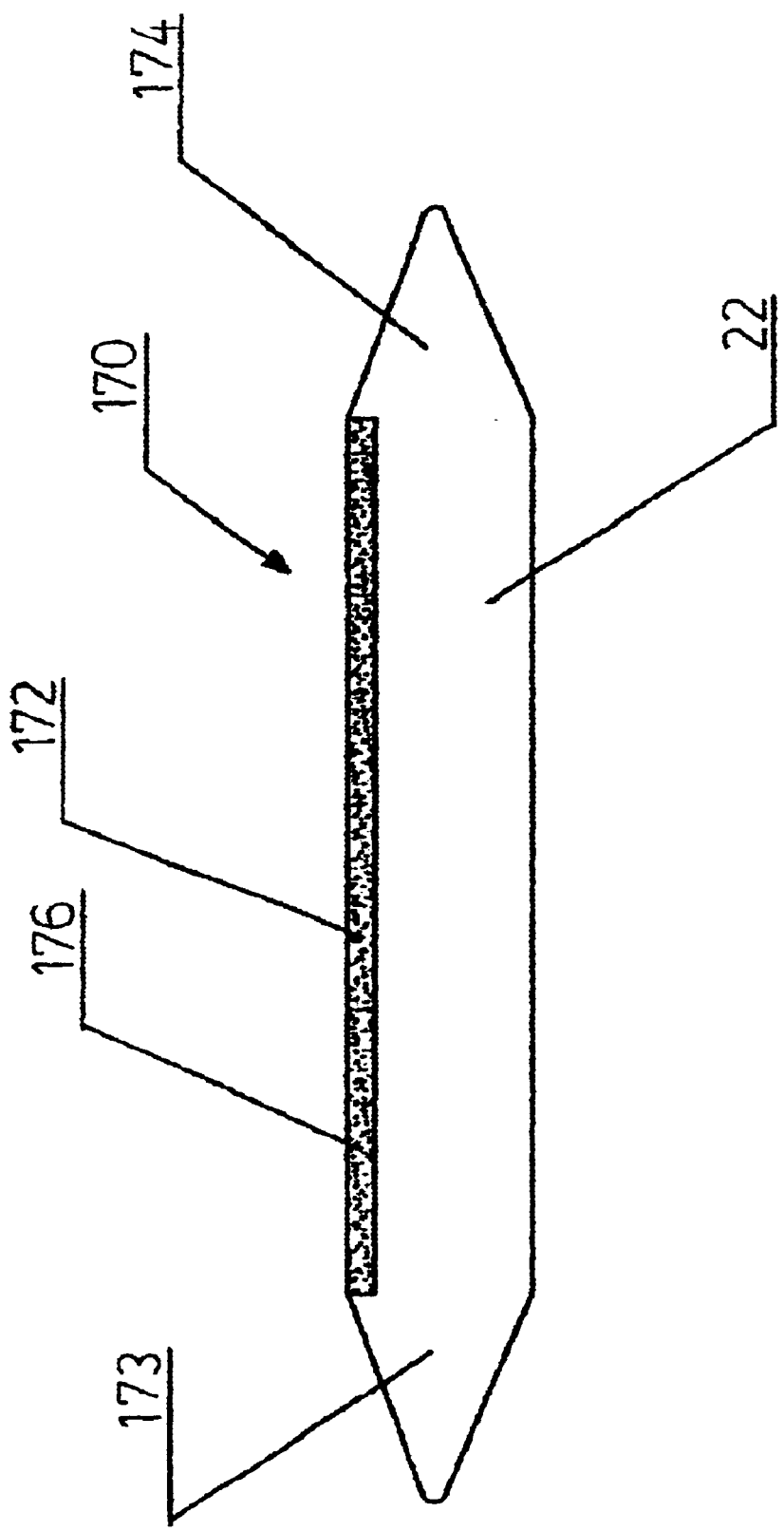
FIG. 11 is a plan view of an outer surface of an alternate version of the cast venting strip.

In the alternative version of the venting device illustrated in FIG. 11, the venting device 170 is the same as that shown in FIGS. 10A and 10B except that the hook array fastener arrangement extending along the upper longitudinal edge comprises an elongate hook array fastener strip 172 that extends at least a substantial portion of the length of the elongate strip of fabric material. As illustrated, the fastener strip 172 extends the entire length of the venting device except for the tapered end sections at 173 and 174. In this version, the fastener strip 172 is preferably made from a stretchable, elastomeric strip of material so that it can stretch with the preferred gauze material forming the strip 22. Fastener strip 172 can be secured by stitching made with elastic threads indicated at 176 to the elongate strip of fabric material. For purposes of the present application, it will be understood that the terms "hook array fastener arrangement" and "hook array fastener strip" as used herein refer to the use of well known and commonly used hook-type fasteners that are used in a variety of other products where fasteners are required. This type of fastener strip is commonly sold under the trademark VELCRO.

In the illustrated preferred venting devices of FIGS. 10A, 10B and 11, there is also a multiple loop array fastener arrangement indicated generally at 180 that extends along the second longitudinal edge section 166 of the elongate strip and that is adapted for attaching to the hook array fastener arrangement 162 or 172. Again, it will be understood that the multiple loop array fastener arrangement can be constructed in a known manner using pads or strips formed with tough, multiple loops on their outer surfaces, which loops will engage readily with and hold on to the numerous small hooks distributed on the surface of the hook array fastener arrangement 162 or on the strip 172. Such loop array fastener arrangements are also commonly available and sold under the trademark VELCRO.

A preferred form of loop array fastener arrangement is illustrated in FIG. 10B wherein there is shown a substantially continuous band of loop array fasteners extending along the second longitudinal edge section and secured thereto by stitching made from elastic threads (not shown but similar to the stitching 176 illustrated in FIG. 11). It will be understood that the illustrated band can be formed by either a continuous, stretchable strip forming the fastener arrangement or by a series of short loop array fastener strips or pads 182, again attached to the fabric by elastic stitching. These pads 182 are separated from one another by transverse joints 184. Where a series of separate pads are used along the second longitudinal edge, these pads or fastener devices need not themselves be made from a stretchable or elastomeric material, sufficient stretchability being provided by the numerous joints 184 and the stretchable or elastic thread used to attach the pads to the elongate fabric material. It will be appreciated that the provision of a substantially continuous band for the loop array fastener arrangement is preferred so that there is no difficulty in attaching the multiple hook array fastener arrangement 162 to the loop array fastener arrangement. for example, due to an inability to match up a particular hook array fastener device with a loop array fastener pad when the venting device has been wound around a body part.

In addition to or in the alternative to the use of elastic threads to attach the VELCRO, such as the pads 182, it is also possible and desirable to use a known type of V-shaped stitching that allows the stitching and the fabric to stretch during use. It is believed unnecessary to illustrate this type of stitch as it is commonly used in garments that must be able to stretch. This known stitching forms a zigzag pattern like the teeth on a standard sawblade.

It should be further appreciated that the use-of a multiple loop array fastener arrangement along the second longitudinal edge section is not always required or preferred, the need for same being dependent upon the particular gauze or fabric material used to form the elongate strip 22. If, for example, the fabric material is sufficiently strong and porous so that it can be readily penetrated by the small hooks of the fastener arrangement at 162, then it will be possible generally to attach the longitudinal edge sections of the venting device together without the use of any loop array fastener arrangement. In such case, the second longitudinal edge section at 166 will simply be left bare on the inside surface so that it is available for securing to the hook array fastener devices. It will also be understood that although square rectangular fastener devices are illustrated in FIGS. 10A and 10B, these fastener devices can also have other configurations, for example, circular or elliptical and these fastener devices can be spaced closer together or further apart than illustrated in FIG. 10A.

Turning now to FIG. 12 of the drawings, this figure illustrates the possibility of connecting together several elongate fabric strips by means of "Velcro" type fastener arrangements. In the illustrated embodiment, there are two end sections or strips 190 and 192 and one straight middle section 194. Although only one middle section 194 is illustrated, it will be appreciated that there can be two or more similar middle sections depending upon the length of the final venting device required for the cast. Each of the three sections 190, 192 and 194 is provided with a hook array fastener arrangement 162 located along its upper longitudinal edge section and arranged on the outer surface. Extending along the inner ends 196 and 198 of the outer end sections are further multiple hook array fastener arrangements indicated at 200 and 202, these fasteners also being on the outer surface. FIG. 12 illustrates two alternate forms for these inner end fasteners. In the fastener arrangement 200, there is a substantially continuous band of multiple hook array fasteners comprising a series of fastener pad or devices 204 separated by joints 206. These fastener pads are preferably attached to the outer surface by means of stitching made of elastic threads and thus some transverse stretching at the inner end 196 is possible. In the fastener arrangement 202, a series of separated hook type fastener pads 208 are distributed along the inner end 198. Spaces 210 are provided between these fastener pads. Arranged on the inner surface of the middle section 194 and located at opposite ends are multiple loop array fastener arrangements 212 and 214. These fastener arrangements can again be either in the form of continuous, elastic fastener strips or they each can be a series of loop array fastener pads or devices. It will be understood that the fastener arrangement 202 can be detachably connected to the fastener arrangement 214 and likewise the hook type fastener arrangement 200 can be detachably connected to the loop type fastener arrangement 212 in order to connect the three sections together. Further, if more than one middle section 194 is to be provided in order to produce a continuous venting device strip, it will be appreciated that some of the middle sections 194 can be provided with multiple hook-array fastener arrangements at opposite ends or they can be provided with a multiple hook array fastener arrangement at one end and a multiple loop array fastener arrangement at the opposite end. The particular type of middle section 194 that is used or provided will be dependent upon the hook or loop type fastener arrangement to which it is to be connected at each end thereof.

Figure 13A:
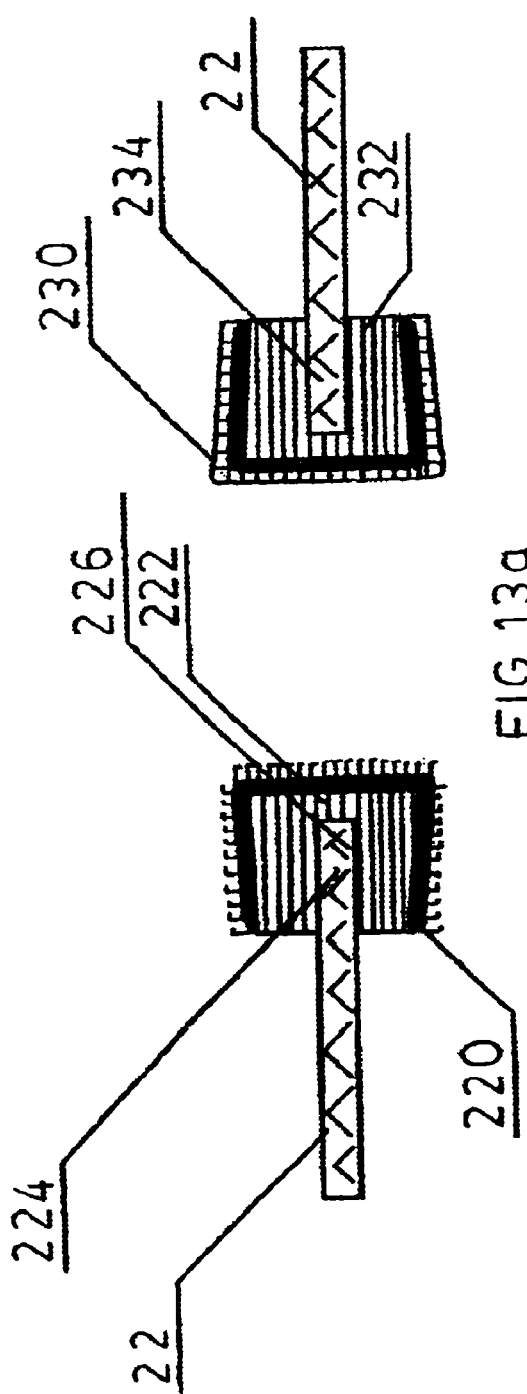
FIG. 13a is a detail sectional view illustrating one preferred method for attaching adjacent longitudinal edges of the venting strip using hook and loop type fastener arrangements.
Figure 13B:
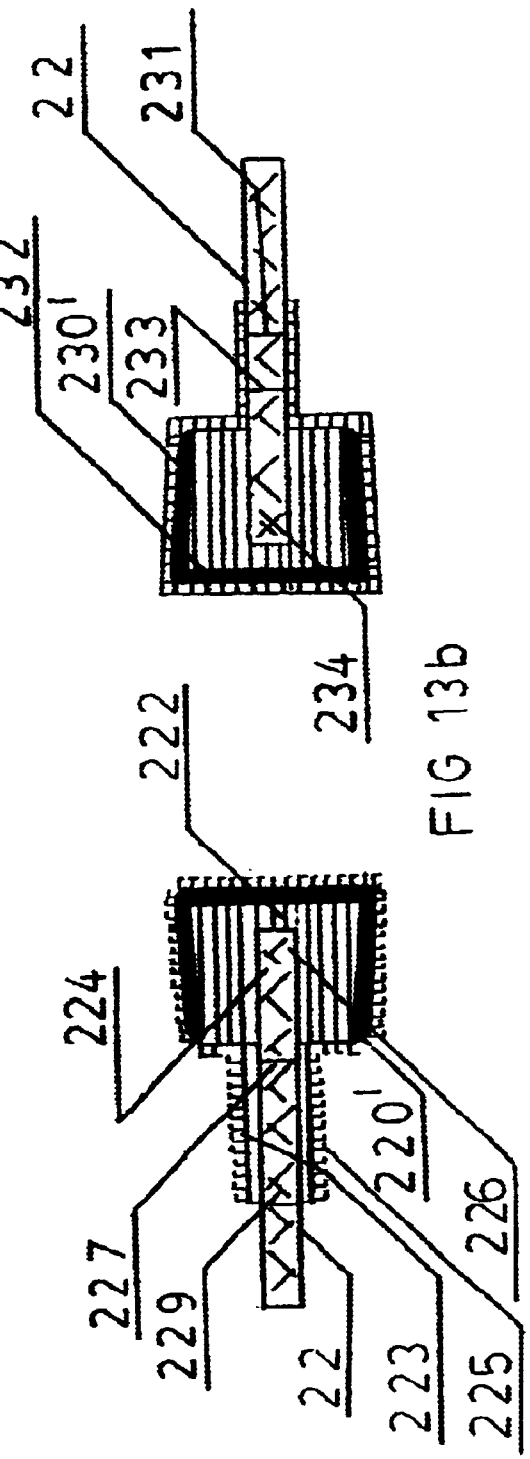
FIG. 13b is a detail sectional view similar to FIG. 13b but illustrating an alternate form of longitudinal edge construction using hook and loop type fastener arrays.

FIGS. 13a and 13b illustrate alternative ways of mounting hook or loop type fastener arrangements along the longitudinal edge or edge section of the elongate strip of porous fabric material or gauze. In the section of the fabric strip shown on the left side of FIG. 13a, there is a multiple hook array fastener arrangement 220 that is supported by an elongate, channel-shaped plastic edge support 222. The fastener arrangement 220 can be bonded by a suitable adhesive to the plastic edge support which in turn can be bounded by adhesive to a longitudinal edge section 224 of the fabric strip. This edge section can be inserted into the channel 226 prior to bonding taking place. It will be understood that the plastic edge support 222 together with the attached fastener arrangement 220 can either be in the form of a continuous, flexible strip extending most or all of the length of the fabric strip 22 or in the form of a series of short strips, for example, only having the length of the individual fastening devices extending along the edge section 164 shown in FIG. 10A. Similarly, a multiple loop array fastener arrangement 230 can be adhesively bonded to another channel-shaped plastic edge support 232 extending along the opposite longitudinal edge of the fabric strip 22. The second longitudinal edge section 234 is placed in the channel and is held therein by a suitable adhesive. Both the hook type fastener arrangement 220 and the loop type fastener arrangement 230 can extend around three sides of the adjacent plastic edge support as shown in FIG. 13a. With this arrangement, even if there is a slight overlap of the adjacent longitudinal edges, these longitudinal edges can still be securely connected together using the hook and loop type fastener arrangements.

Instead of using adhesive to bond the plastic edge supports to the fabric strip, it is also possible to mold these plastic strips in place on the longitudinal edges so that they are securely held on these edges by the molding process. The hook or loop type fastener arrangement can then be subsequently bonded to the plastic edge support after it has been molded and has hardened.

On the left side of the version illustrated in FIG. 13b there is a wider multiple hook array fastener arrangement 220' that is supported by plastic edge support 222 and a longitudinal edge section of the strip 22. The fastener arrangement 220' can again be bonded to the plastic edge support but the flat sections 223 and 225 can be attached to the fabric by a longitudinal line of stitching at 227. There can be a second line of stitching at 229. Similarly, on the right side of this version there is a wider multiple loop fastener arrangement 230' that is adhesively bonded to the edge support 232 and is also connected by stitching at 233 to a longitudinal edge section of the strip 22. Additional stitching 231 at the inner edge of the fastener arrangement can also be provided.

Figure 14:
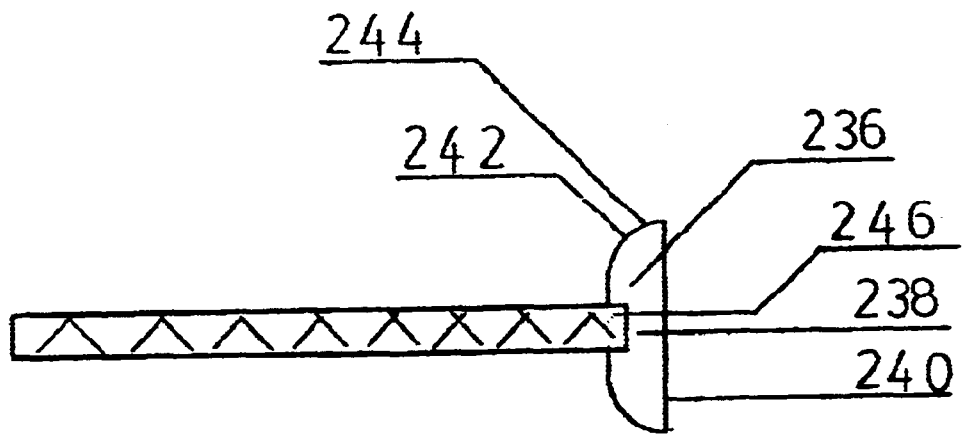
FIG. 14 is a cross-sectional detail of a longitudinal edge construction for the venting strip illustrating one form of plastic edge support for a hook or loop type fastener array (not shown)
Figure 15:
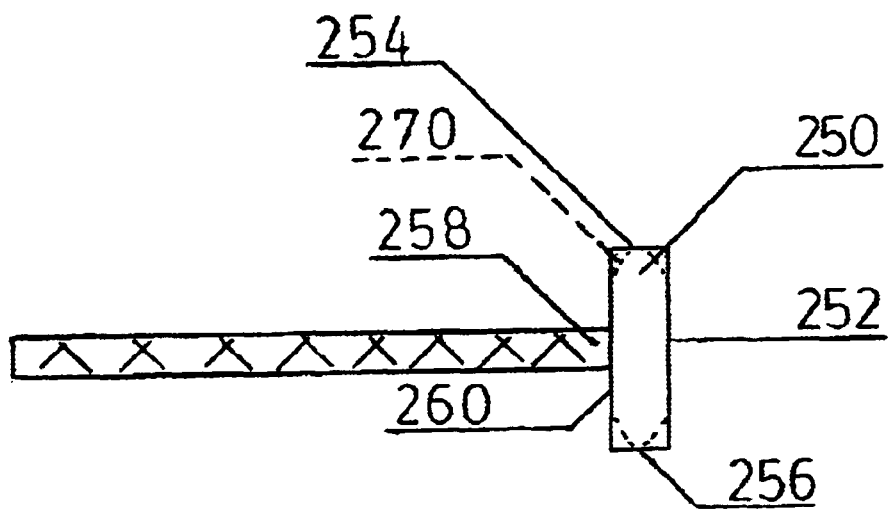
FIG. 15 is a cross-sectional detail similar to FIG. 14 but showing another form of plastic edge support.
Figure 16:
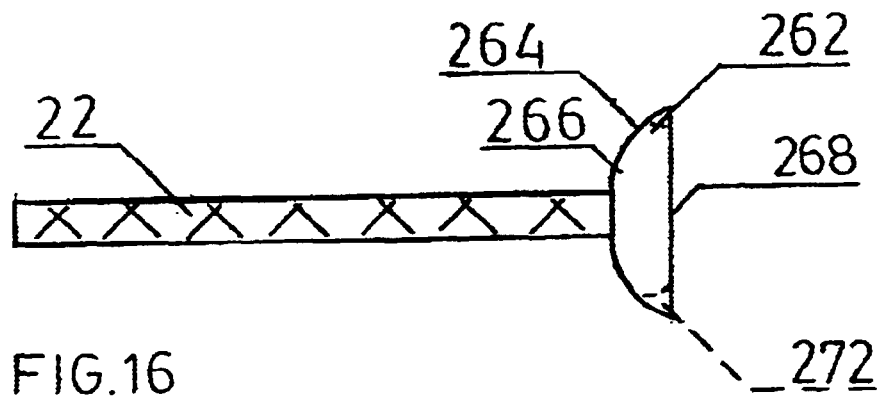
FIG. 16 is a further cross-sectional detail similar to FIG. 14 but showing a further version of the plastic edge support.

FIGS. 14 to 16 illustrate alternative cross-sections for the plastic edge supports to which the hook or loop type fastener arrangement can be bonded. In the embodiment of FIG. 14, the edge support 236 has only a very shallow groove at 238 and, opposite this groove, is a flat outer side 240. Extending between the shallow groove and the side 240 are upper and lower curved sides 242 and 244. Again, adhesive can be used to bond the edge 246 to the plastic edge support. The edge support 236 could also be made without any shallow groove 238 (as per the versions of FIGS. 15 and 16 described below).

The plastic edge support 250 of FIG. 15 has a substantially rectangular cross section with a flat outer side 252 and no channel formed in the opposite side. The top and bottom sides 254 and 256 of the edge support are substantially narrower than the width of the outer side 252. With this edge support, the edge of the fabric strip at 258 is bonded directly to flat inner side 260. It is also possible to make this version 250 with an attachment groove in the side 260 similar to the groove 238.

The edge support 262 shown in FIG. 16 is somewhat similar to the edge support 250 as it has no channel to receive the edge of the fabric strip. However, with this edge support, there are upper and lower curved sides 264 and 266 that extend between the longitudinal edge of the fabric strip 22 and a flat, elongate outer side 268. It is also possible to make the support 262 with an attachment groove similar to the groove 238 where the curved sides 264 and 266 meet. In FIGS. 14 to 16, the hook or loop type fastener arrangement has been omitted but it will be understood that this arrangement is bonded to at least the outer side of the plastic edge support and optionally on the curved or flat outer and top surfaces as well. Also, instead of sharp corners or edges extending along the length of the plastic edge support, it is also possible to round the longitudinally extending edges as indicated by the dash lines 270 in FIG. 15 and the dash lines 272 in FIG. 16.

Figure 17:
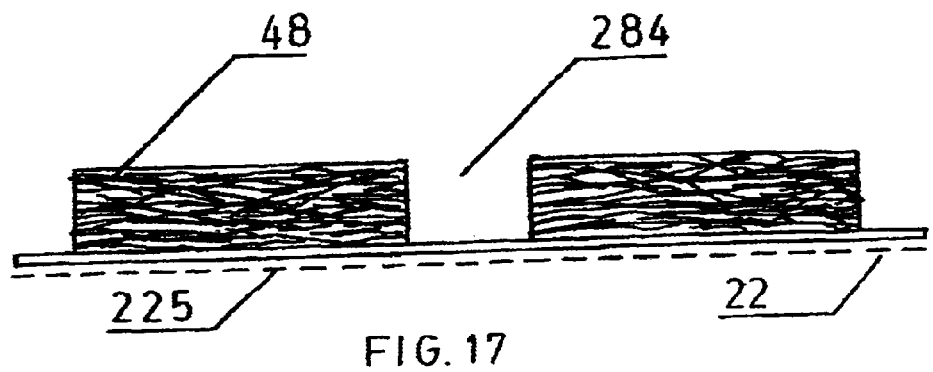
FIG. 17 is a detail edge view showing a portion of another embodiment of the venting device, this embodiment having aerating devices in the form of a layer of non-woven, plastic threads.
Figure 18:
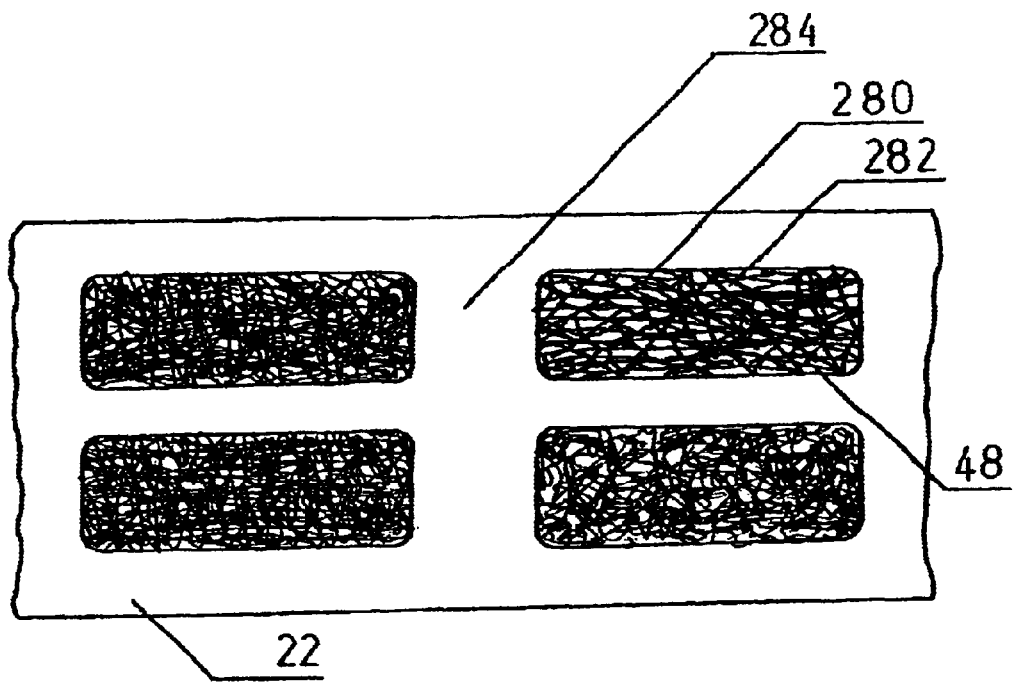
FIG. 18 is a top view of the small section of the venting device shown in FIG. 17.

The plastic aerating devices affixed to and located on the inner surface of the venting device can take various forms other than the elongate plastic tubes illustrated in FIGS. 1 and 2. One alternate form of aerating device is illustrated in FIGS. 17 and 18. These aerating devices are flexible layers 48 of interconnected, non-woven plastic threads or strips 280. Each layer has numerous small air passageways indicated at 282 that are formed therein. The thickness of each layer can be only one quarter inch or less and the layers can be separated by longitudinally and transversely extending air gaps 284. The layers are again adhesively bonded to a strip of fabric material 22 and it will be understood that the layers 48 are arranged on the inner surface of this material. The layers 48 have a consistency or makeup similar to natural "loofah" commonly used as a body sponge or body cleaning product. However, the layers 48 are made sufficient thin and they are provided with sufficiently large air spaces between the plastic threads that each layer is flexible and is able to bend to the body contour.

Although the illustrated layers are rectangular in shape, other shapes are also possible, including square, triangular and elongate strips. Also, the size of each layer and the size and number of air gaps between the layers can vary depending upon the flexibility of each layer and the proposed use for the particular venting device. Preferably the venting device employing these layers 48 is sufficiently stretchable to be permit it to be pulled snugly around the body part and the arrangement of the layers 48 must be sufficiently flexible as well to permit the venting device to adjust itself closely to the contour of the body prior to application of the cast material.

Figure 19:
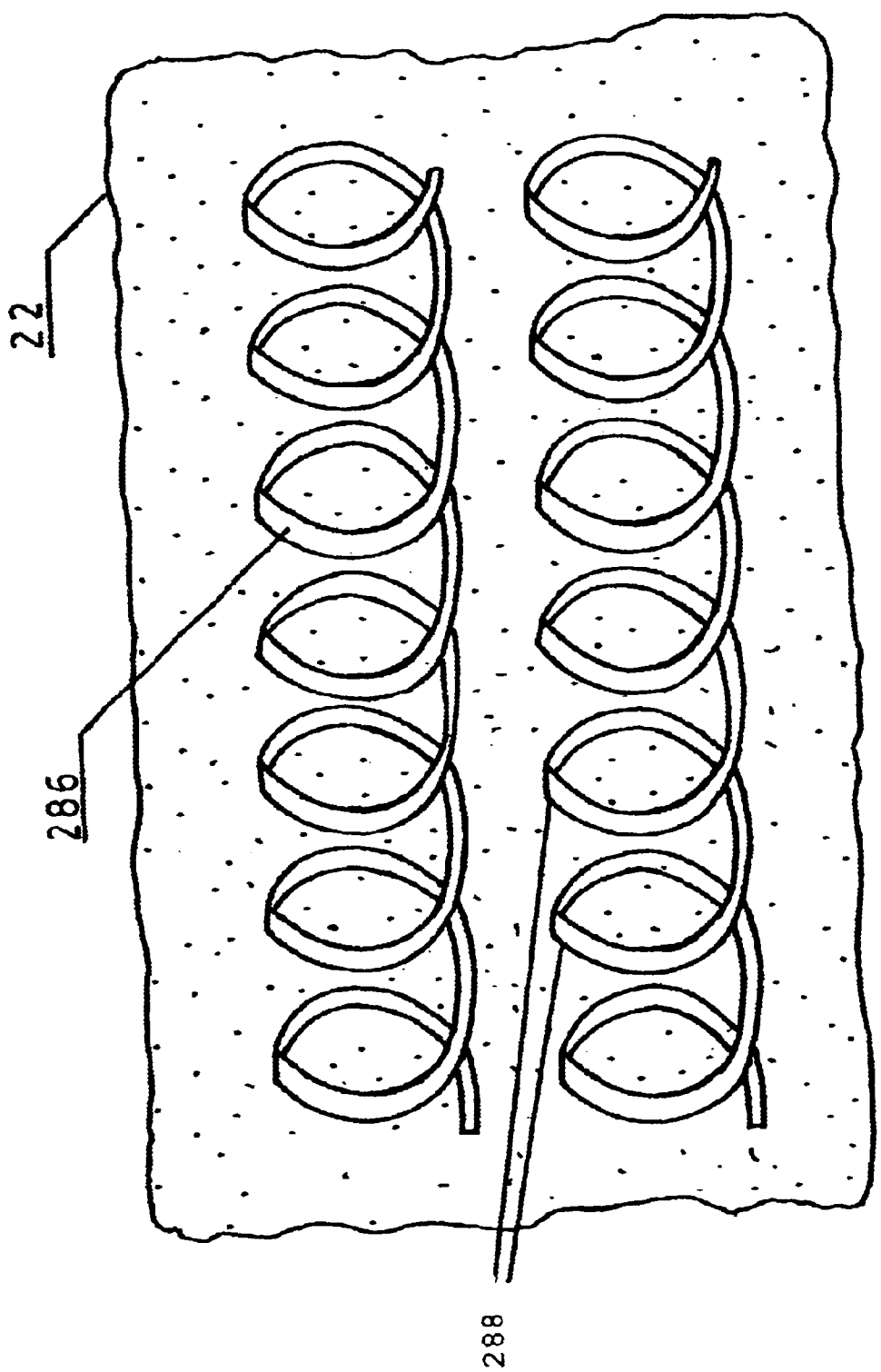
FIG. 19 is a plan view similar to FIG. 18 but showing a further manner of constructing a venting device in accordance with the invention.

Another form of aerating devices is illustrated in FIG. 19 which shows only a portion of the inner surface of the venting device in the form of a fabric strip 22. In this version, the aerating devices comprise a substantial number of spiral-shaped, resilient plastic members 286 which are distributed over the inner surface of the venting device. The spiral shaped members can extend in a longitudinal direction of the venting device, but preferably extend transversely to the elongate strip of fabric. Each of the plastic members 286 is close to but spaced apart from adjacent ones of these members 286. The members preferably have a maximum exterior diameter less than one half inch and preferably no more than one quarter inch. The thread or wire from which member 286 is formed should have sufficient diameter or thickness that it will not irritate or cut a patient's skin when the venting device is put in place. Furthermore, adjacent individual spirals 288 should be reasonably closely spaced, again so they will not irritate or cut into the patient's skin, which may be sensitive and also so that the member 286 can adequately support the surrounding rigid cast without collapsing under the applied force.

Figure 20:
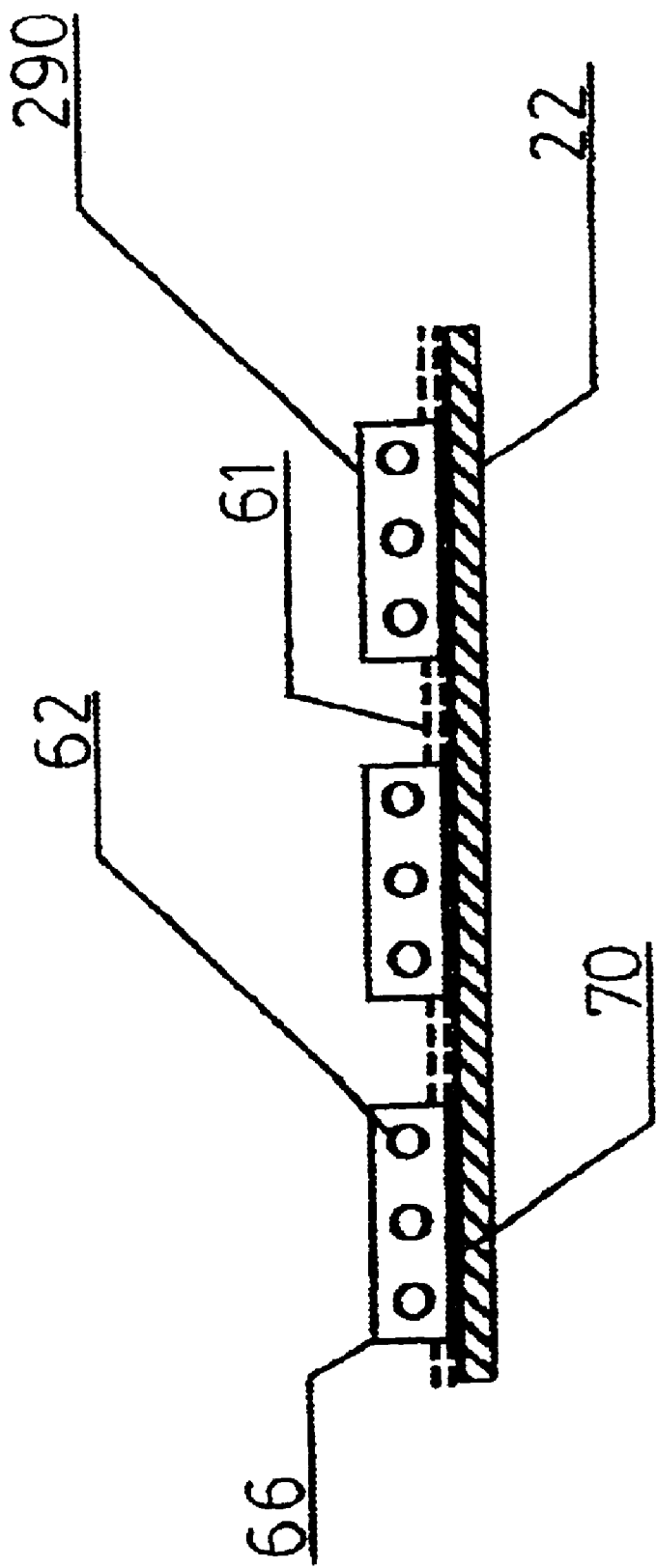
FIG. 20 is a detail view of a section of still another embodiment of the venting device, this version employing plastic ring members.
Figure 21:
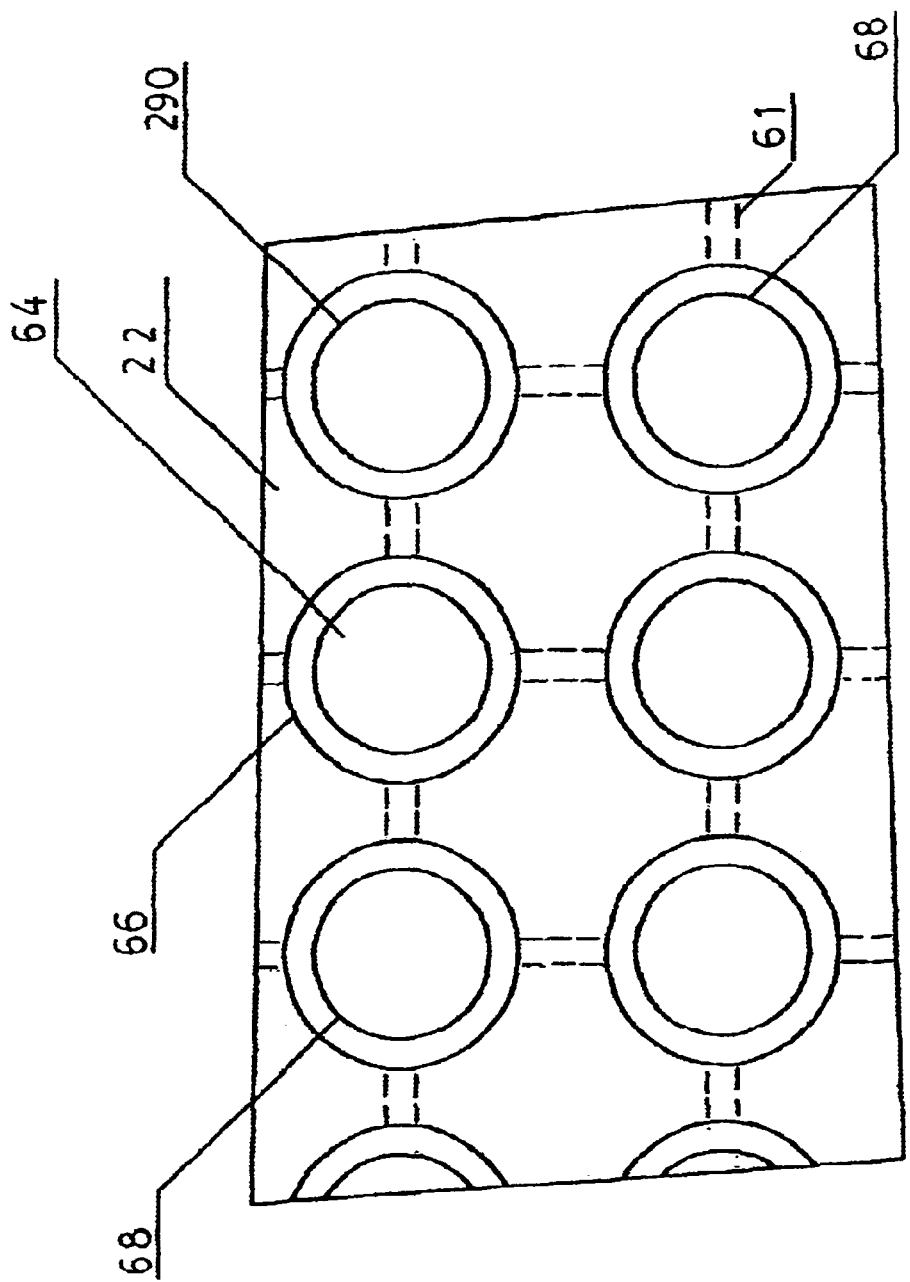
FIG. 21 is a plan view of the section of the venting device shown in FIG. 20.

Turning now to a further embodiment of the venting device, this embodiment being illustrated in FIGS. 20 and 21, the plastic members which are affixed to the fabric strip 22 are in the form of ring-like plastic members 290, each of which is perforated with a number of small holes 62 about its perimeter. These holes permit the passage of air to and from a circular space 64 located inside each ring-like member. The plastic members 290 are distributed evenly or substantially uniformly over the inner surface of the fabric strip. The size of the member 290 can vary and will depend to some extent on the particular use to which the venting device is to be put. Typically, the preferred exterior diameter of each ring-like member is no more than one inch and more preferably is no more than one half inch. The thickness or depth of each ringlike member can also vary but preferably is no more than one quarter inch. The outer, annular edges of each member 290, these edges being indicated at 66, can be rounded if desired to avoid unnecessary irritation of the user's skin and to make the wearing of the venting device as comfortable as possible. The annular interior edges 68 can also be rounded, if desired. Again, it will be understood that the members 290 are preferably bonded by a suitable medical adhesive indicated at 70. If desired, the ring-like members 290 can be attached to the fabric material or gauze in a manner similar to the elongate tubular members, this procedure being described hereinafter in conjunction with FIG. 33 of the drawings.

Optionally, the ring-like members 290 can be interconnected by integral plastic web connectors 61 illustrated in dashed lines in FIGS. 20 and 21. These web connectors can interconnect adjacent members 290 in order to maintain the uniform spacing of the members, particularly before they are bonded to the fabric. The plastic connectors 61 help support the ring-like members 290 even after the latter have been bonded to the fabric and help to prevent the ring-like members from becoming detached or from becoming displaced from their desired position. If desired, these thin plastic connectors can be broken in order to provide the venting device with sufficient flexibility and stretchability when it is being applied to the body part.

Figure 22:
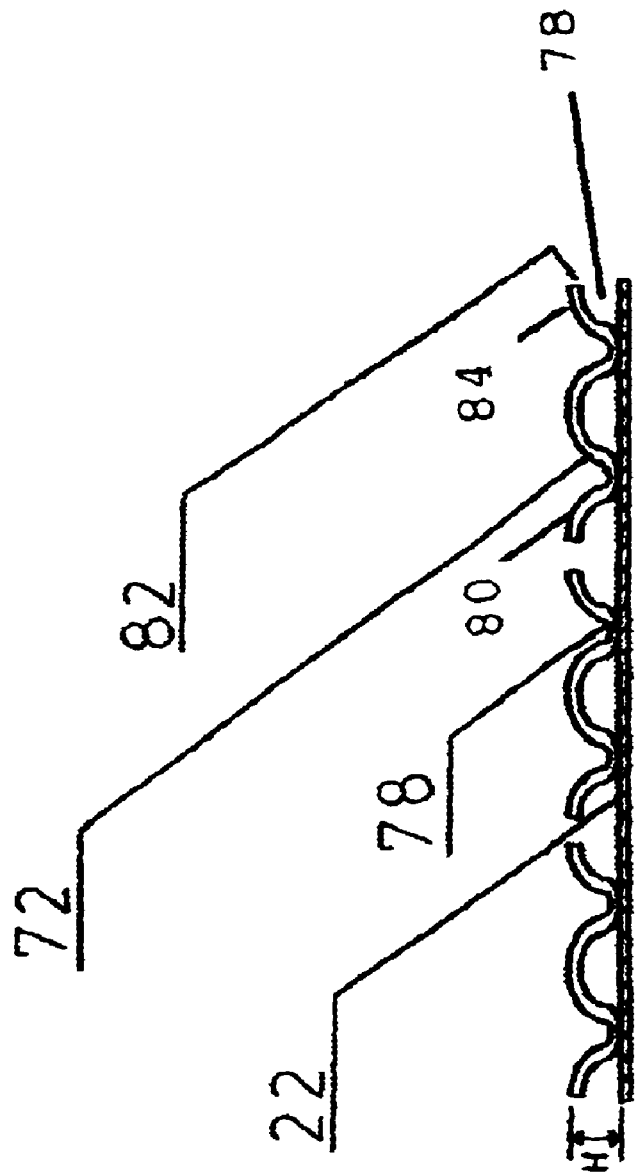
FIG. 22 is an edge view of a small section of a further embodiment of the venting device, this version employing corrugated plastic members.
Figure 23:
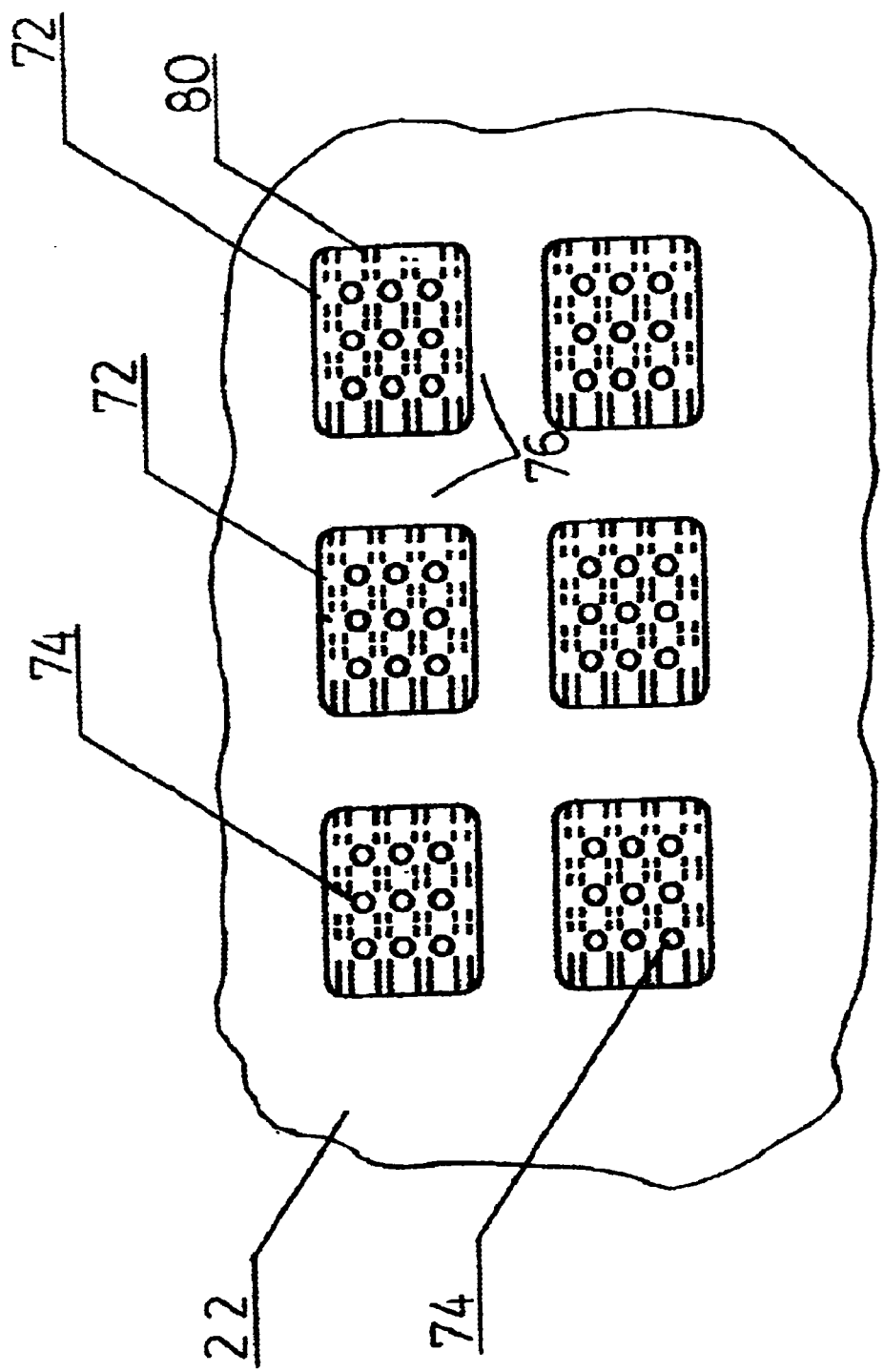
FIG. 23 is a plan view of the small section of the venting device shown in FIG. 22.

FIGS. 22 and 23 illustrate yet another version of the venting device of the invention, this version using aerating devices that are affixed to the inner surface of the fabric strip 22 and that are in the form of at least several and preferably a substantial number of corrugated plastic members 72, each of which is perforated with a substantial number of small holes 74. These holes can be circular and can be as small as ¹⁄₁₆th inch or less in diameter. These holes tend to increase the circulation of air about the corrugated members. The members 72 are distributed preferably uniformly over the inner surface of the fabric strip 22. Also, these members are preferably separated by longitudinally and transversely extending air gaps 76, the width of which can vary but preferably these gaps should be sufficiently wide to allow adequate air flow between the corrugated members and they should not be so wide as to allow contact between the rigid cast material and the patient's skin. Preferably the width of the gap is less than ½inch while the preferred height H of each corrugated member 72 is no more than ¼inch.

The members 72 are preferably affixed by a suitable medical adhesive indicated at 78. Preferably the opposite edges 80 and 82 are rounded to avoid irritation to adjacent skin and the edge region 84 forming each of the edges 80 and 82 should not extend towards the skin but should either extend parallel to the adjacent skin as shown or extend away from the skin. Although only a couple of corrugations are shown on the illustrated plastic member 72, it will be appreciated that these members could have more corrugations such as four or five or more, particularly if the corrugations are made quite small in width.

Figure 24:
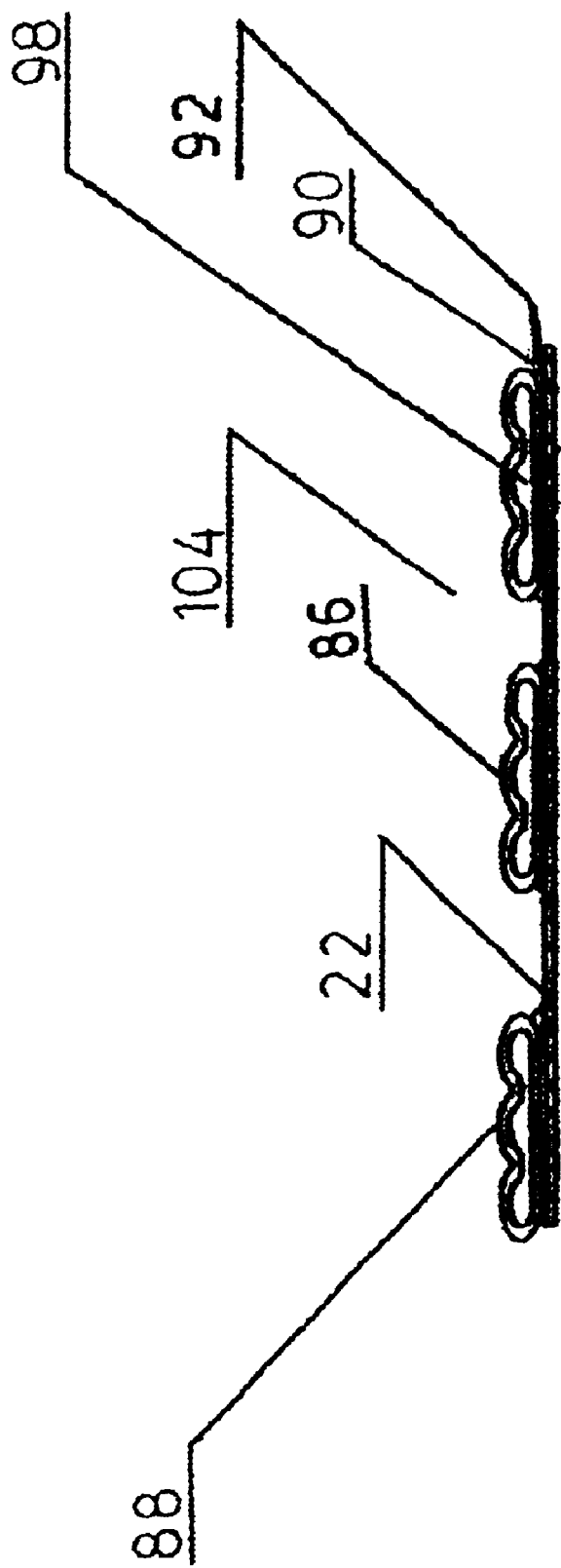
FIG. 24 is an edge view of part of another embodiment of the venting device, this version employing plastic members with corrugated tops.
Figure 25:
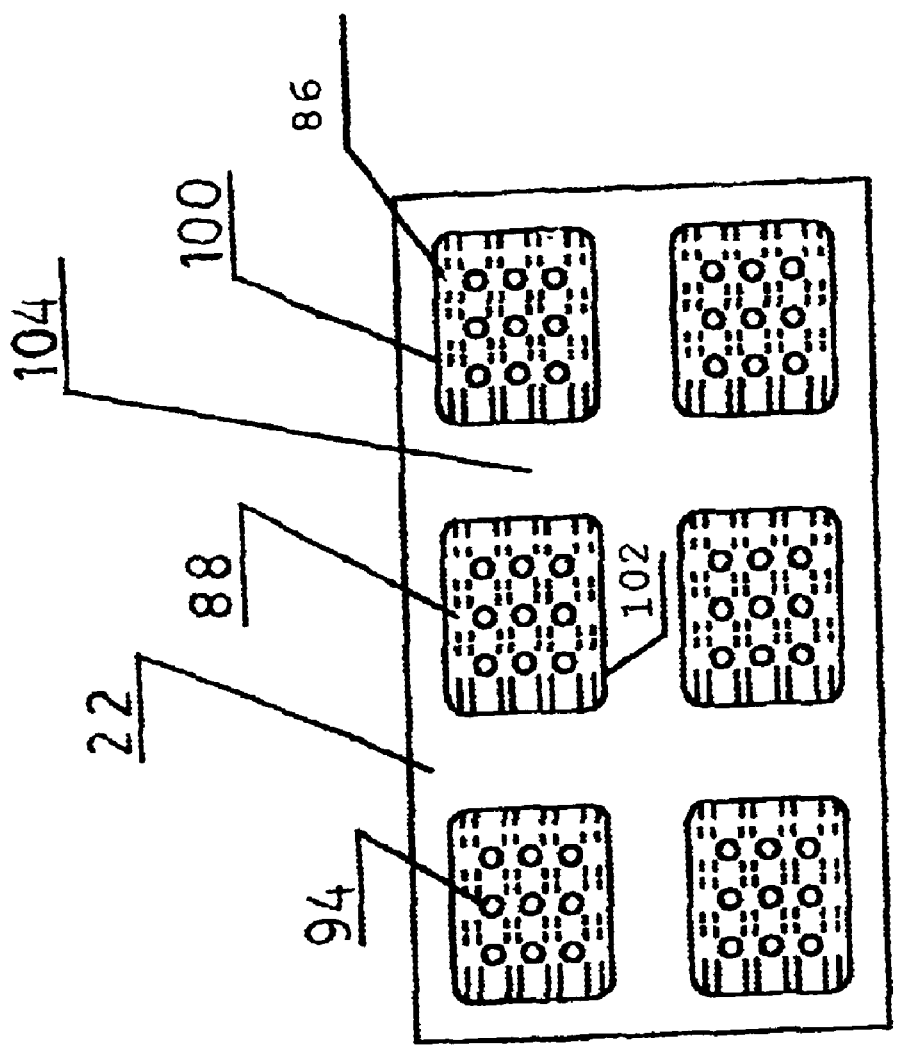
FIG. 25 is a plan view of the section of the venting device shown in FIG. 24.

Still another type of aerating device for the venting device of the invention is illustrated in FIGS. 24 and 25. These aerating devices which are affixed to the inner surface of the fabric strip 22 are also corrugated plastic members but these members 86 have corrugated top sections 88 and planar bottoms 90 integrally connected to the top sections. The bottoms 90 are affixed by means of a suitable adhesive 92 to the porous fabric material or gauze. The top sections 88 are perforated with a substantial number of small holes 94 which can be round. These holes open into an air space 98 formed between each top section and its respective bottom 90. It will be understood that each corrugated member 86 is preferably open-ended at 100 and 102.

The corrugated members 86 are spaced apart by longitudinally and transversely extending air gaps 104 which are sufficiently wide to permit the free flow of air between the members 86 and which are not so wide as to allow contact between the surrounding rigid cast and the patient's skin. Preferably the maximum width of the air gaps 104 is less than ½inch. The dimensions and height of each corrugated member 86 can be similar to the corrugated members illustrated in FIGS. 22 and 23.

Figure 26:
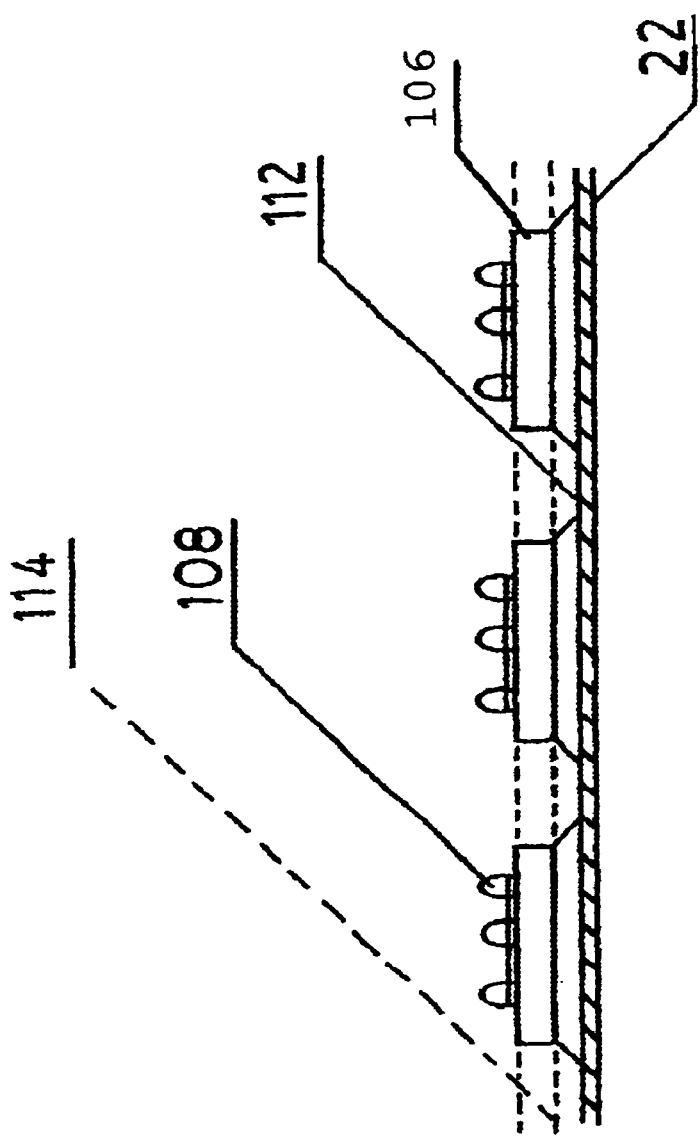
FIG. 26 is an edge view of still another embodiment of the venting device, this version employing a grid of plastic members with a number of bumps formed on their top surfaces.
Figure 27:
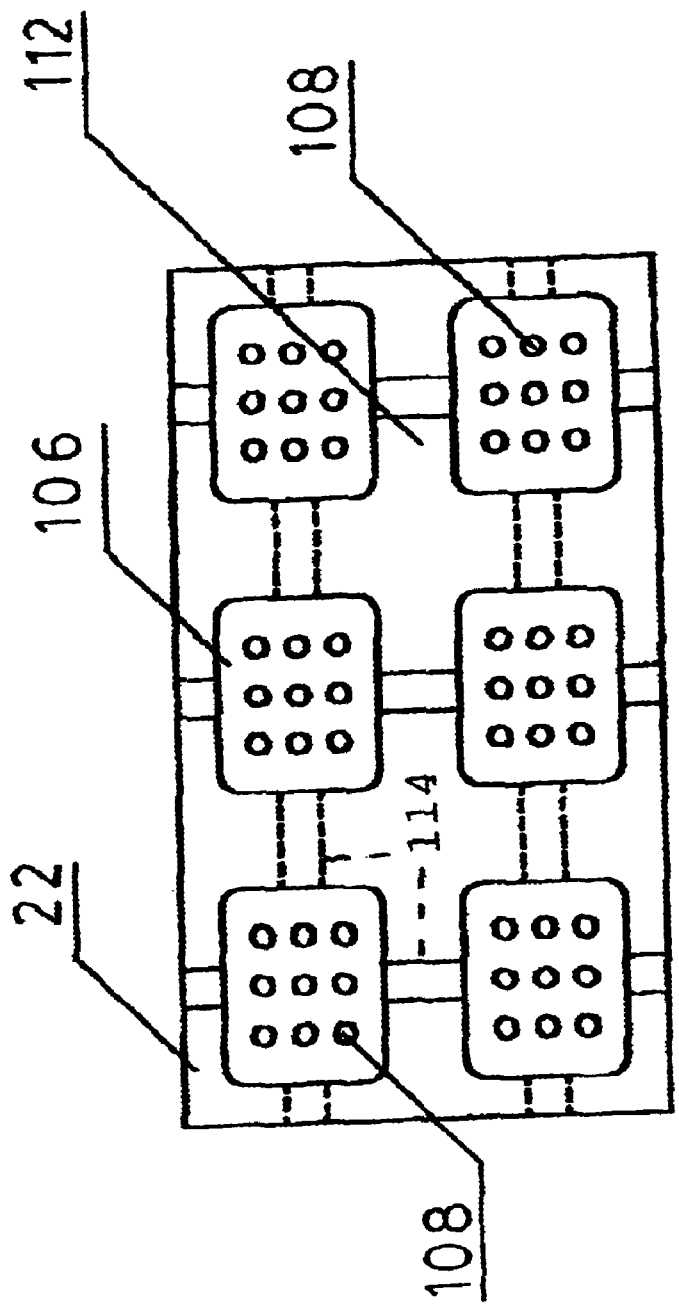
FIG. 27 is a plan view of the section of the venting device shown in FIG. 26.

Yet another form of aerating device for the surgical cast venting device of the invention is illustrated in FIGS. 26 and 27. In this embodiment, the aerating devices affixed to the inner surface of the fabric strip comprise at least several and preferably a substantial number of plastic members 106 with at least several and preferably a substantial number of bumps or protrubences 108 formed on an outer surface 110 of the plastic member. The bumps, which are preferably rounded as shown, project away from the inner surface of the fabric strip 22. The plastic members, which can have a square shape as shown, are preferably distributed evenly over the inner surface of the strip and are spaced apart from one another. There are longitudinally and transversely extending air gaps 112 extending between the plastic members. These gaps can be similar in width to the air gaps 76 and 104 of the embodiments illustrated in FIGS. 22 to 25. Although the illustrated members have a generally square shape, they can also have a rectangular, triangular, or rounded shape. Although the members have twenty-five bumps 108 laid out in a regular grid on the outer surface, the number of bumps can be fewer or more than the number shown.

Optionally, the plastic members 106 can be interconnected by means of thin, plastic connecting members 114 which can be readily broken, if required. The connectors 114 can be formed integrally with the plastic members 106 in the molding process. By using these connectors, the plastic members 106 will be correctly spaced and oriented prior to bonding and as they are bonded by adhesive to the fabric strip. Again, after the members have been bonded to the fabric material, the thin plastic connectors 114 can be readily broken, if necessary, to provide the venting device with the desired stretchability and flexibility for mounting on a body part.

Figure 28:
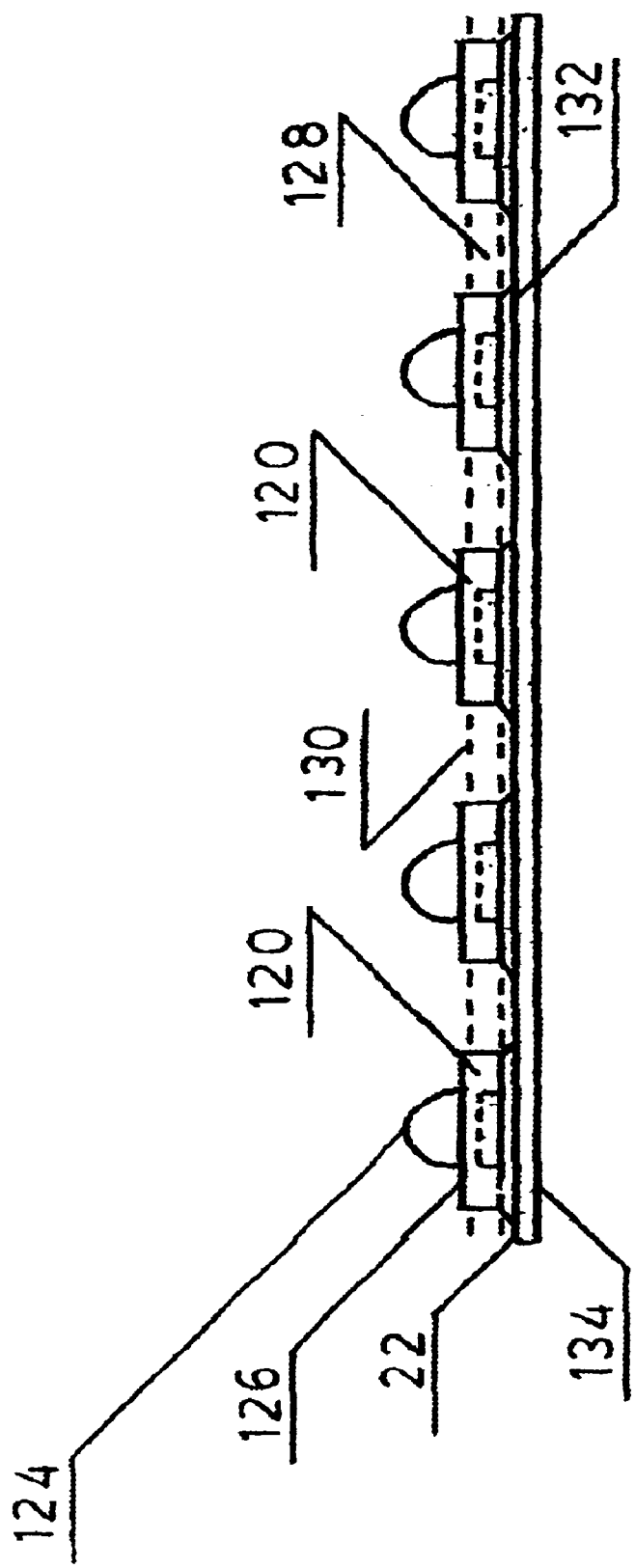
FIG. 28 is an edge view of part of another venting device of the invention, this embodiment employing a grid work of small plastic members having a bump formed in each of their top surfaces.
Figure 29:
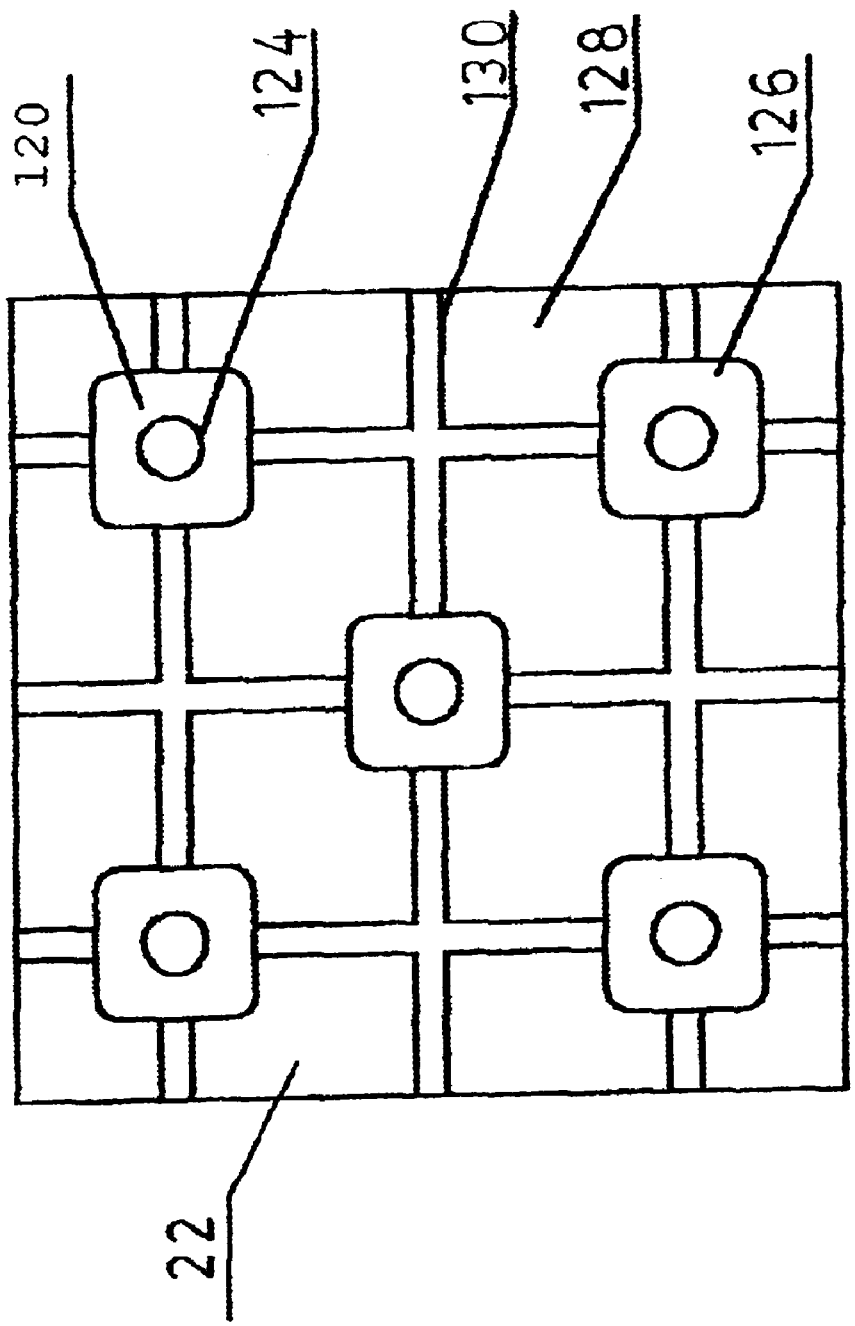
FIG. 29 is a detail view of the section shown in FIG. 28.

Yet another form of aerating device for use in the venting device is illustrated in FIGS. 28 and 29. In this version, the plastic aerating devices fixed to the inner surface of the fabric strip 22 are at least several and preferably a substantial number of plastic members 120 which can be quite small and relatively closely spaced. Unlike the members shown in FIGS. 26 and 27, each of the members 120 is formed with a single bump or protuberance 124 which is preferably rounded and centrally located on the outer surface 126. This single bump projects away from the inner surface of the fabric material. The plastic members 120 are uniformly distributed over the inner surface and are spaced apart from one another by longitudinally and transversely extending air gaps 128.

As in the previous embodiment, the members 120 can be optionally interconnected using integral connecting plastic webs or links 130 shown in dash lines in FIG. 28 but in solid lines in FIG. 29. These webs help to maintain the spacing in between the plastic members 120 and to maintain their orientation before they are bonded to the fabric material by adhesive. The adhesive 132 is applied to the outer surface 134 of the fabric and soaks through the fabric material to the adjacent surface of the plastic member 120 before being cured and dried. The web members 130 can readily be broken to give the venting device adequate flexibility and to permit the device to be stretched around the body part.

Figure 30:
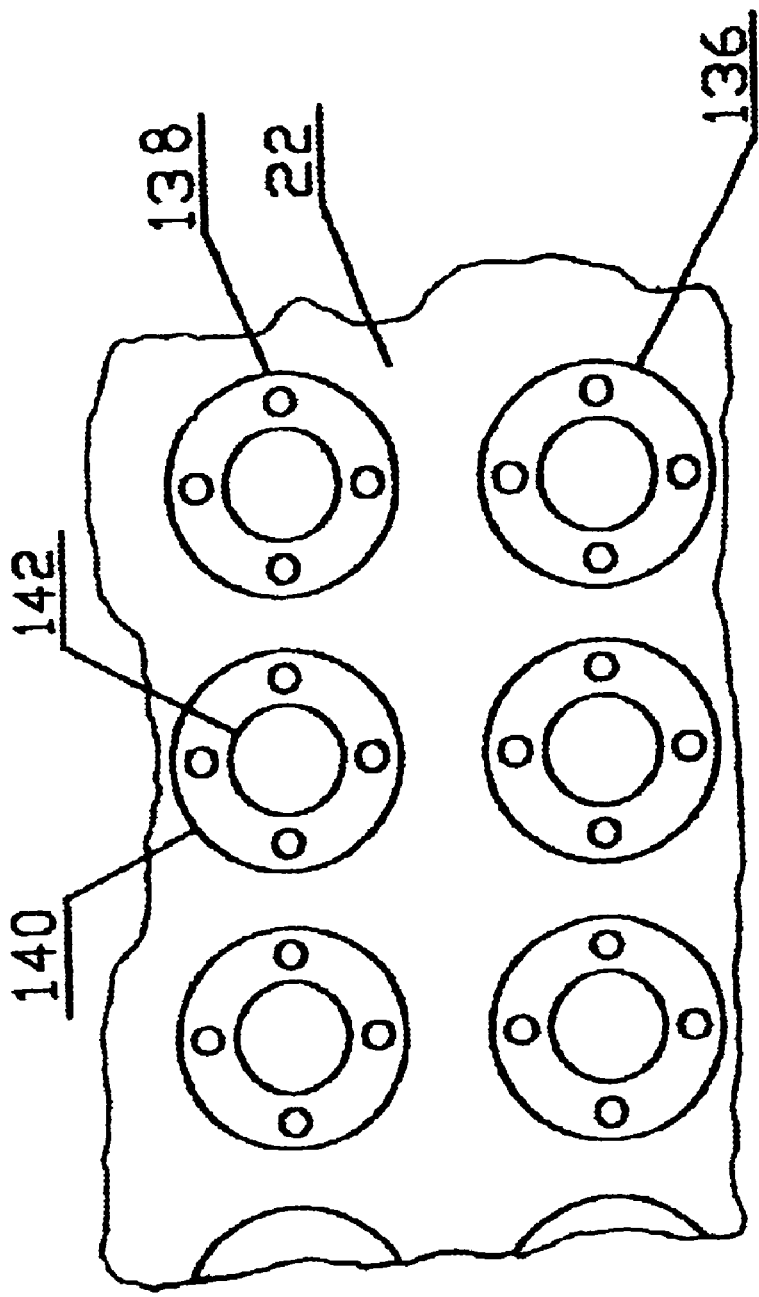
FIG. 30 is a detail plan view of part of an inner surface of a further embodiment of the venting device.

Another version of an aerating device is illustrated in FIG. 30 wherein the aerating devices affixed to the inner surface of the strip 22 comprise a substantial number of ring-like plastic members 136 which are perforated with small holes 138. Although only four holes 138 are shown in each member in FIG. 30 for ease of illustration, it will be appreciated that the members 136 can have more small holes such as eight or more. The provision of the holes helps to reduce the area of the fabric material that is actually covered by the plastic of the ring members. The annular inner and outer edges 140 of each ring-like member can be rounded to help lessen skin irritation by these members. The size of these members can be approximately the same size as the ring-like members 290 illustrated in FIGS. 20 and 21. Also, instead of being round members as illustrated, the members 136 could instead be oval-shaped or even square or rectangular in shape.

Another form of aerating device similar to the plastic tubular members first described is illustrated in FIG. 31. In this version, there are again elongate tubular members but these plastic members 150 are somewhat flattened rather than being round in cross-section. In other words, these members 150 have an oval-shaped cross-section and because they can then be larger in size, they can have more small holes 152 formed in their sides. Otherwise the construction of this version of the venting device is substantially the same as the earlier described version such as that shown in FIGS. 1 and 2. Again, the plastic members 150 extend parallel to one another and are spaced apart generally a uniform distance. They are affixed by a suitable medical adhesive indicated at 154 to the fabric strip 22.

Figure 32:
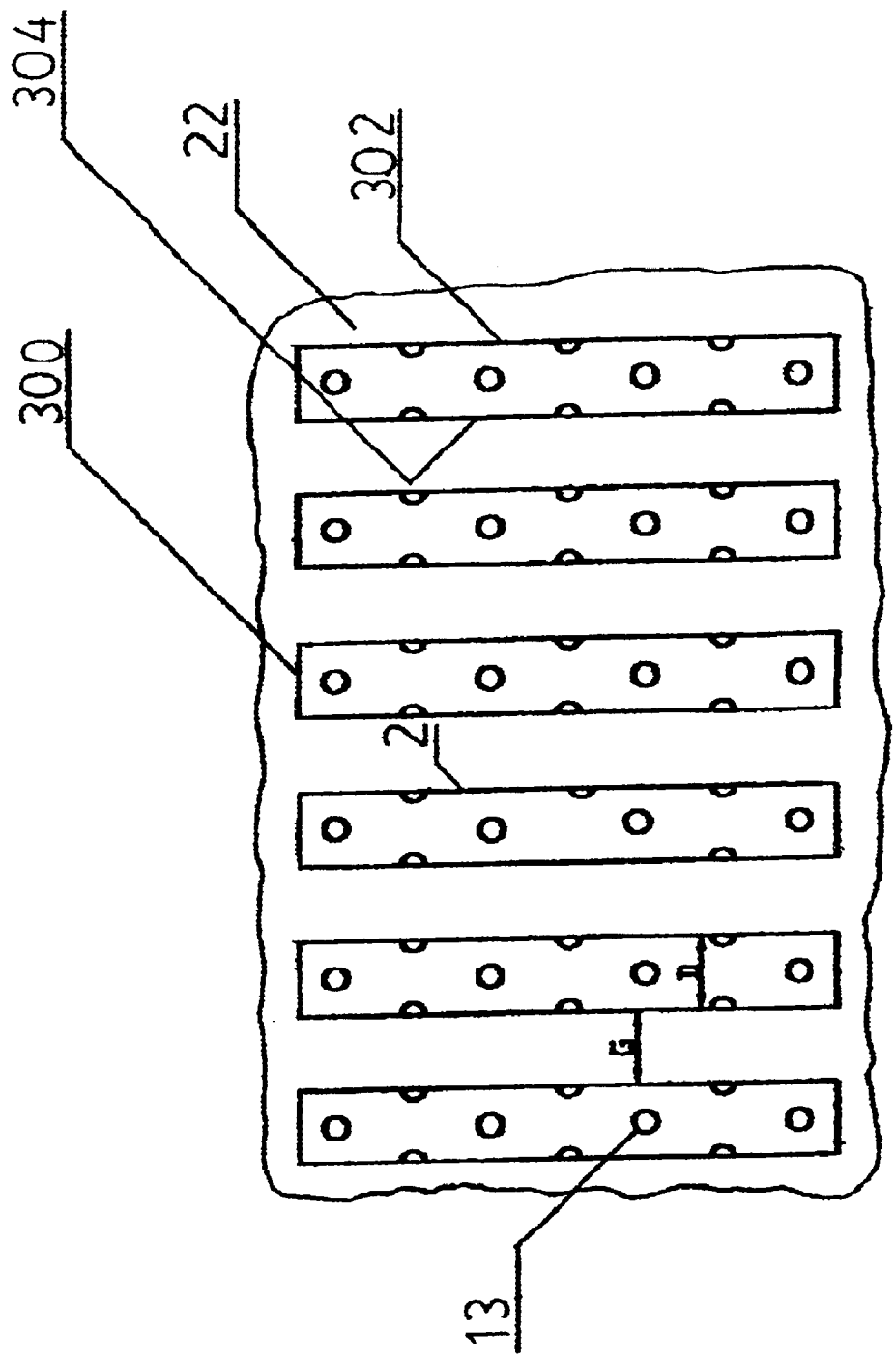
FIG. 32 is a detail view showing a portion of the inner surface of a venting device similar to that shown in FIG. 2, this portion being shown flat for ease of illustration.

FIG. 32 illustrates some further details concerning the construction of the preferred cast venting device which uses a substantial number of plastic tubular members 2 distributed over and affixed to the inner surface of the fabric strip 22. Preferably, each of these tubular members is open ended at both ends thereof including the end 300 illustrated in FIG. 32. For some applications of the venting strip and depending also on the nature of the plastic tubular member itself, the tubular member could be constructed with only one open end while still providing adequate ventilation under the cast.

Preferably the plastic tubular members 2 are elongate as illustrated in FIG. 32 and are adhesively bonded to the fabric material. The preferred adhesive is, as indicated, a non-toxic medical adhesive which is known in the medical art and which will bond to both the flexible plastic of the tubular members and the fabric material which is preferably cotton gauze.

The ventilation holes 13 can be round as shown and quite small, for example, ¹⁄₁₆inch or less. There should be holes on the side of the tubular member opposite the fabric material and also on the two rounded sides indicated at 302 and 304 in FIG. 32 that are located at 90 degrees approximately to the aforementioned side. This arrangement enables air to pass freely into and out of the tubular members. Preferably the plastic from which the tubular members are made is a medical grade plastic and is selected so as to be as compatible with the skin as possible and non-allergenic. The plastic must also be sufficiently flexible to mold itself to the contour of the limb when the venting device is applied, particularly when the exterior cast material is being or has been applied about the venting device.

Preferably each plastic tubular member is located close to but spaced apart from adjacent ones of the plastic tubular members as illustrated in FIG. 32. For example, the gap G indicated in FIG. 32 which may be substantially uniform can be approximately equal to the diameter D of the adjacent tubular members. A smaller relative gap is also possible but the gap should be sufficient to allow adequate air flow in the longitudinal direction between the tubular members. Also, the gap G should not be too large in order that the tubular members can act as proper spacers to maintain the rigid cast material away from the adjacent skin area. In other words, the gap should not be so large that when the cast is applied, there is in effect no air gap in some locations between the skin and the rigid cast layer.

Another advantageous optional feature that can be employed in the venting devices of the invention is that of making the fabric material or layer 22 from thread or fibers having a distinctive color other than white or off-white. Preferably the fabric material is made with a bright color such as green or blue. By making the fabric material with a color that is distinctively different from the white plaster of paris material that forms the hard cast, a medical technician or doctor removing the cast by means of a saw or other cutting tool will easily know when the tool has passed through the hard cast material and has contacted the venting device. This will be revealed by colored fibers being thrown out or removed by the cutting device. The technician or doctor will then know that it is not necessary to cut any deeper in that region of the cast. This feature lessens the risk of the patient being inadvertently cut by the cutting tool.

Figure 33:
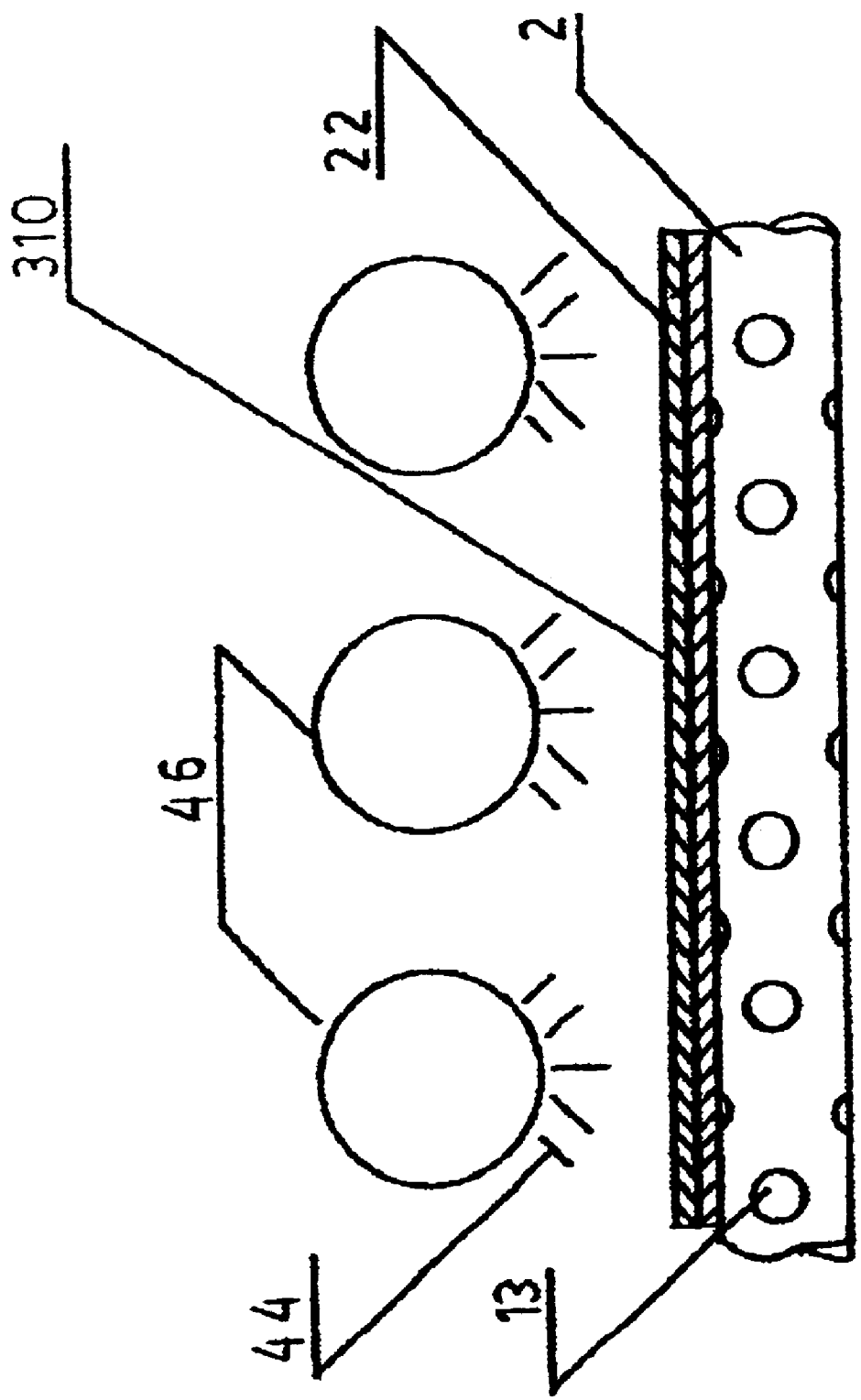
FIG. 33 is a detail edge view of a portion of the venting device of FIG. 1 or FIG. 2 illustrating the manner in which the tubular members can be adhered to the porous fabric.

FIG. 33 illustrates a preferred method for attaching either the plastic tubular members shown or other forms of aerating devices described above to the strip of fabric material. The individual tubular members 2 can be placed in a suitable holder of the required shape so that they can be held in their correct relative positions for the bonding process. With the tubular members correctly positioned, the fabric layer or strip 22 is placed over the holder and the tubular members and then a suitable medical adhesive is applied to the outer surface 310 of the fabric along attachment areas directly opposite the tubular members or other aerating devices. Because of the porous nature of the fabric material or gauze, the adhesive soaks through the fabric to the tubular members at which point the adhesive is cured by exposure to ultraviolet light indicated schematically at 44 which can be created by ultraviolet light bulbs or tubes 46 arranged about the top surface of the fabric material.

Figure 34:
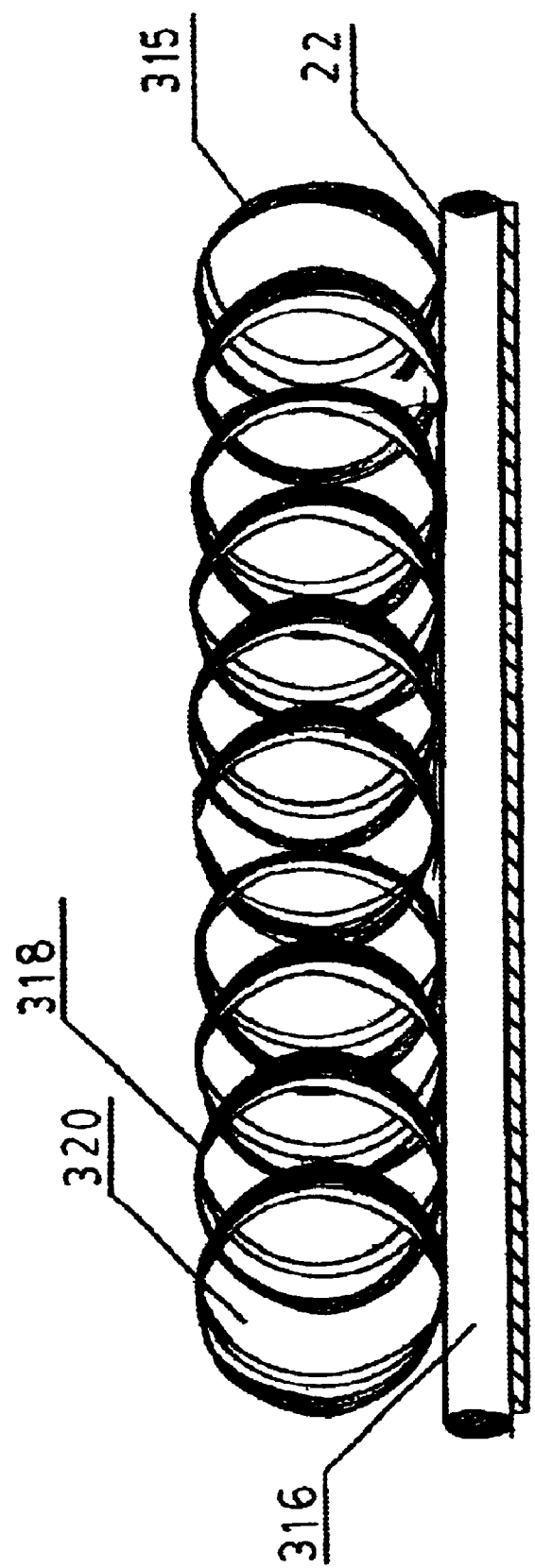
FIG. 34 is a side detail view illustrating another form of tube that can be used in the venting device of the invention.

FIGS. 34 and 35 illustrate another possible form of plastic tubing member that can be used in the venting device of the invention. In this version each tubular member 315 has a substantially semi-cylindrical bottom half 316 which can be made of imperforate solid plastic or which can be perforated with circular holes (not shown) as per the embodiment shown in FIG. 32. However, the upper half (that is the half located furthest from the fabric strip 22) comprises a series of strong, durable plastic threads 318 that criss-cross one another as shown to form a semi-cylindrical arc that is sufficiently strong to maintain its shape during use of the venting strip. It will be appreciated that this arrangement leaves many holes or apertures 320 in the upper half through which air can pass and circulate. The plastic threads form an open "sieve-like" arrangement along the length of each tubular member 315.

It will be appreciated by those skilled in the art that various modifications and changes can be made to the described and illustrated surgical cast venting devices without departing from the spirit and scope of the invention. Accordingly, all such modifications and changes as fall within the scope of the appended claims are intended to be part of this invention.

I claim:

1. A surgical cast venting device comprising:
   an elongate strip of porous fabric material having an inner side and an outer side;
   a plurality of elongate plastic tubing members distributed over and attached to said elongate strip on said inner side thereof, said tubing members each extending substantially parallel to said inner side and being open ended, said tubing members each having holes distributed along their respective lengths so as to permit the passage of air in and out of the tubing members; and
   sponge material attached to said tubing members and extending about the exterior of said tubing members,
   wherein said elongate strip is adapted for winding around part of a human's body or an animal's body prior to application of a surgical cast over said part of the body.

2. A surgical cast venting device according to claim 1 wherein said plastic tubing members are relatively short.

3. A surgical cast venting device according to claim 2 wherein said elongate strip is tapered at opposite ends thereof and said plastic tubing members are attached at a small acute angle to a transverse line perpendicular to a longitudinal central axis of the elongate strip.

4. A surgical cast venting device according to claim 2 wherein for a substantial portion of the length of the elongate strip, said plastic tubing members extend from one long edge of the strip a distance which does not exceed one-half the width of the strip.

5. A surgical cast venting device according to claim 4 wherein said elongate strip is tapered at opposite ends thereof and said plastic tubing members each are bonded by adhesive to said elongate strip.

6. A surgical cast venting device according to claim 2 including a multiple hook array fastener arrangement that extends along and is attached to a first longitudinal edge section of said elongate strip and that is adapted to detachably secure said longitudinal edge section to an adjacent second longitudinal edge section of the elongate strip when said elongate strip is wound around said part of the body.

7. A surgical cast venting device according to claim 6 including a multiple loop array fastener arrangement that extends along said second longitudinal section of the elongate strip and that is adapted for attaching to said hook array fastener arrangement.

8. A surgical cast venting device according to claim 6 wherein said porous fabric material is gauze.

9. A surgical cast venting device according to claim 8 wherein said hook array fastener arrangement comprises a series of spaced apart, hook array fastener devices distributed along said first longitudinal edge section and adhesively bonded to said first longitudinal edge section.

10. A surgical cast venting device according to claim 6 wherein said hook array fastener arrangement comprises an elongate hook array fastener strip that extends at least a substantial portion of the length of said elongate strip of fabric material and that is secured by stitching made with elastic threads to said elongate strip of fabric material.

11. A surgical cast venting device comprising:
   an elongate porous woven fabric strip; and
   a plurality of flexible, elongate plastic tubes with holes distributed along their respective lengths, said tubes being distributed along the length of and attached to said fabric strip on one side thereof, each tube extending lengthwise in a direction substantially parallel to said one side and extending transversely to the length of said fabric strip, said tubes being arranged so that their longitudinal central axes are substantially parallel to each other when said fabric strip is laid flat and straight and so that the tubes are located over an area that extends widthwise from one longitudinal edge of the fabric strip to a longitudinal line located no more than one-half the maximum width of the fabric strip from said one longitudinal edge,
   wherein said elongate strip is suitable for winding around part of a human's body or an animal's body prior to application of a surgical cast over said part of the body.

12. A surgical cast venting device according to claim 11 wherein said elongate strip is tapered at opposite ends thereof and said tubes are attached at a small acute angle to a transverse line perpendicular to a longitudinal centreline of the elongate strip.

13. A surgical cast venting device according to claim 11 including means for securing said fabric strip in place after said fabric strip has been wound around said part of the body.

14. A surgical cast venting device according to claim 11 wherein said elongate tubes are evenly distributed over an area that extends widthwise from said one longitudinal edge of the fabric strip to said longitudinal line which is located about one-third the maximum width of said fabric strip from said one longitudinal edge.

15. A surgical cast venting device according to claim 11 including a multiple hook array fastener arrangement that extends along and is attached to a first longitudinal edge section of said elongate strip and that is adapted to detachably secure said longitudinal edge section to an adjacent second longitudinal edge section of the elongate strip when said elongate strip is wound around said part of the body.

16. A surgical cast venting device according to claim 15 including a multiple loop array fastener arrangement that extends along said second longitudinal edge section of the elongate strip and that is adapted for attaching to said hook array fastener arrangement.

17. A surgical cast venting device according to claim 15 wherein said fabric strip comprises a cotton gauze material.

18. A surgical cast venting device comprising:
   an elongate porous fabric strip having two opposite ends, having two opposite, longitudinal side edge sections, and having inner and outer surfaces;
   plastic aerating devices adhesively bonded to and located on said inner surface, said aerating devices covering at least a major portion of said inner surface in a substantially uniform manner and comprising flexible layers of interconnected non-woven plastic threads, each aerating device having numerous, small air passageways formed therein; and
   a multiple hook array fastener arrangement that extends along and is secured to a first of said longitudinal side edge sections and that is adapted to detachably secure said first longitudinal side edge section to a second of said longitudinal side edge sections when said fabric strip is wound around part of a human's body or an animal's body prior to application of a surgical cast over said part of the body.

19. A venting device according to claim 18 wherein said aerating devices are flexible layers of interconnected non-woven plastic threads, each having numerous, small air passageways formed therein.

20. A venting device according to claim 18 including a multiple loop array fastener arrangement that extends along said second longitudinal side edge section and that is adapted for attaching to said hook array fastener arrangement.

21. A venting device according to claim 18 wherein said fabric strip comprises a gauze material.

22. A venting device according to claim 18 wherein said hook array fastener arrangement comprises an elongate hook array fastener strip that is stretchable and extends at least a substantial portion of the length of said fabric strip, and wherein said fastener strip is secured by stitching made with elastic threads to said fabric strip.

23. A venting device according to claim 18 wherein said hook array fastener arrangement comprises a series of spaced-apart, hook array fastener devices distributed along said first longitudinal edge section and adhesively bonded to said first longitudinal edge section.

24. A surgical cast venting device comprising:
   an elongate porous fabric strip having two opposite ends, having two opposite, longitudinal side edge sections, and having inner and outer surfaces;
   plastic aerating devices adhesively bonded to and located on said inner surface, said aerating devices covering at least a major portion of said inner surface in a substantially uniform manner, said aerating devices comprising a substantial number of spiral-shaped, resilient plastic members distributed over said inner surface of the fabric strip and each close to but spaced apart from adjacent ones of the resilient plastic; and
   a multiple hook array fastener arrangement that extends along and is secured to a first of said longitudinal side edge sections and that is adapted to detachably secure said first longitudinal side edge section to a second of said longitudinal side edge sections when said fabric strip is wound around part of a human's body or an animal's body prior to application of a surgical cast over said part of the body.

25. A surgical cast venting device comprising:
   an elongate porous fabric strip having two opposite ends, having two opposite, longitudinal side edge sections, and having inner and outer surfaces;
   plastic aerating devices adhesively bonded to and located on said inner surface, said aerating devices covering at least a major portion of said inner surface in a substantially uniform manner, said aerating devices comprising a substantial number of plastic members with one or more bumps formed on an outer surface of each plastic member, said one or more bumps projecting away from said inner surface of the fabric strip, said plastic members being spaced apart from one another; and
   a multiple hook array fastener arrangement that extends along and is secured to a first of said longitudinal side edge sections and that is adapted to detachably secure said first longitudinal side edge section to a second of said longitudinal side edge sections when said fabric strip is wound around part of a human's body or an animal's body prior to application of a surgical cast over said part of the body.

26. A surgical cast venting device comprising:

an elongate, flexible strip of thin porous material having an inner side and an outer side;

a plurality of relatively short, elongate tubing members distributed over and mounted on said elongate strip on said inner side thereof, the length of each tubing member extending substantially parallel to said inner side, each tubing member having a plurality of aerating holes distributed along its length; and sponge material attached to said tubing members and extending about the exterior of said tubing members, wherein said flexible strip with said tubing members is adapted for winding around part of a human's body or an animal's body prior to application of a surgical cast over said part of the body.

27. A venting device according to claim 26 including a multiple hook array fastener arrangement that extends along and is attached to a first longitudinal edge section of the flexible strip and that is adapted to detachably secure said longitudinal edge section to an adjacent second longitudinal edge section of the flexible strip when the flexible strip is wound around said part of the body.

* * * * *